US009414785B2

(12) United States Patent
Nagata et al.

(10) Patent No.: US 9,414,785 B2
(45) Date of Patent: *Aug. 16, 2016

(54) GARMENT FOR BIOINFORMATION MEASUREMENT HAVING ELECTRODE, BIOINFORMATION MEASUREMENT SYSTEM AND BIOINFORMATION MEASUREMENT DEVICE, AND DEVICE CONTROL METHOD

(71) Applicant: Nihon Kohden Corporation, Tokyo (JP)

(72) Inventors: Shinya Nagata, Osaka (JP); Ryuji Nagai, Osaka (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,280

(22) Filed: Apr. 9, 2015

(65) Prior Publication Data
US 2015/0223756 A1 Aug. 13, 2015

Related U.S. Application Data

(62) Division of application No. 10/599,169, filed as application No. PCT/JP2005/005393 on Mar. 24, 2005, now Pat. No. 9,026,200.

(30) Foreign Application Priority Data

Mar. 24, 2004 (JP) .................................. 2004-086110

(51) Int. Cl.
*A61B 5/00* (2006.01)
*A61B 5/0456* (2006.01)
(Continued)

(52) U.S. Cl.
CPC ............... *A61B 5/6804* (2013.01); *A61B 5/044* (2013.01); *A61B 5/04012* (2013.01);
(Continued)

(58) Field of Classification Search
None
See application file for complete search history.

(56) References Cited

U.S. PATENT DOCUMENTS 276,078 A 4/1883 Rittig
3,268,845 A 8/1966 Whitmore
(Continued)

FOREIGN PATENT DOCUMENTS

CN 86104798 5/1987
EP 0782837 7/1997
(Continued)

OTHER PUBLICATIONS

U.S. Appl. No. 14/682,260, filed Apr. 9, 2015, Nagata et al.
(Continued)

*Primary Examiner* — Brian T Gedeon
(74) *Attorney, Agent, or Firm* — Jason H. Vick; Sheridan Ross, PC

(57) ABSTRACT

One embodiment provides a garment for measuring biological information, a measurement system, a measurement device and a method of controlling thereof capable of measuring biological information with accuracy regardless of variations of each examinee. When an examinee wears a shirt, four limb electrodes are arranged at positions so that the electrodes cover the body surface other than around the clavicle. At that time, the four limb electrodes are assigned to positions so that they cover about the pelvis. Also, during the use of the shirt, chest electrodes cover from the body surface (around lower part of left side of the body) of a presternal region around the left thorax in a perpendicular direction of the body axis (a direction perpendicular to the length of the shirt) and the electrodes are assigned so as to cover from the body surface around the fourth rib to that around the sixth rib.

6 Claims, 27 Drawing Sheets

(51) Int. Cl.
  *A61B 5/08* (2006.01)
  *A61B 5/0408* (2006.01)
  *A61B 5/04* (2006.01)
  *A61B 5/0432* (2006.01)
  *A61B 5/044* (2006.01)
  *A61B 5/0452* (2006.01)

(52) U.S. Cl.
  CPC ............ *A61B 5/0432* (2013.01); *A61B 5/0456* (2013.01); *A61B 5/04085* (2013.01); *A61B 5/04525* (2013.01); *A61B 5/0816* (2013.01); *A61B 5/6805* (2013.01); *A61B 5/7203* (2013.01); *A61B 5/742* (2013.01); *A61B 2560/0468* (2013.01); *A61B 2562/0209* (2013.01)

(56) References Cited

U.S. PATENT DOCUMENTS

| | | | |
|---|---|---|---|
| 3,483,861 | A | 12/1969 | Tiep |
| 4,308,872 | A | 1/1982 | Watson et al. |
| 4,494,553 | A | 1/1985 | Sciarra et al. |
| 4,580,572 | A | 4/1986 | Granek et al. |
| 4,583,553 | A | 4/1986 | Shah et al. |
| 4,608,987 | A | 9/1986 | Mills |
| 4,733,670 | A | 3/1988 | Hays et al. |
| 4,784,162 | A | 11/1988 | Ricks et al. |
| 4,809,699 | A | 3/1989 | Shimizu et al. |
| 4,815,473 | A | 3/1989 | Watson et al. |
| 4,817,625 | A | 4/1989 | Miles |
| 4,827,943 | A | 5/1989 | Bornn et al. |
| 4,832,038 | A | 5/1989 | Arai et al. |
| 4,889,131 | A | 12/1989 | Salem et al. |
| 4,909,260 | A | 3/1990 | Salem et al. |
| 4,960,118 | A | 10/1990 | Pennock |
| 4,966,155 | A | 10/1990 | Jackson |
| 5,131,399 | A | 7/1992 | Sciarra et al. |
| 5,178,151 | A | 1/1993 | Sackner |
| 5,191,893 | A | 3/1993 | Reiten |
| 5,224,479 | A | 7/1993 | Sekine |
| 5,241,300 | A | 8/1993 | Buschmann |
| 5,295,490 | A | 3/1994 | Dodakian |
| 5,348,008 | A | 9/1994 | Bornn et al. |
| 5,353,793 | A | 10/1994 | Bornn |
| 5,423,328 | A | 6/1995 | Gavish |
| 5,439,002 | A | 8/1995 | Narimatsu et al. |
| 5,454,376 | A | 10/1995 | Stephens et al. |
| 5,467,768 | A | 11/1995 | Suda et al. |
| 5,564,429 | A | 10/1996 | Bornn et al. |
| 5,588,425 | A | 12/1996 | Sackner et al. |
| 5,704,351 | A | 1/1998 | Mortara et al. |
| 5,749,365 | A | 5/1998 | Magill |
| 5,868,671 | A | 2/1999 | Mahoney |
| 5,937,854 | A | 8/1999 | Stenzler |
| 6,047,203 | A | 4/2000 | Sackner et al. |
| 6,287,264 | B1 | 9/2001 | Hoffman |
| 6,341,229 | B1 | 1/2002 | Akiva |
| 6,381,482 | B1 | 4/2002 | Jayaraman et al. |
| 6,424,860 | B1 | 7/2002 | Karlsson et al. |
| 6,453,186 | B1 | 9/2002 | Lovejoy et al. |
| 6,551,252 | B2 * | 4/2003 | Sackner ............... A61B 5/0205 600/301 |
| 6,687,523 | B1 | 2/2004 | Jayaramen et al. |
| 6,723,055 | B2 | 4/2004 | Hoffman |
| 6,783,498 | B2 | 8/2004 | Sackner et al. |
| 6,945,941 | B2 | 9/2005 | Eriksen et al. |
| 7,094,206 | B2 | 8/2006 | Hoffman |
| 7,207,948 | B2 | 4/2007 | Coyle |
| 7,245,956 | B2 | 7/2007 | Matthews et al. |
| 7,251,524 | B1 | 7/2007 | Hepp et al. |
| 7,267,652 | B2 | 9/2007 | Coyle et al. |
| 8,668,653 | B2 | 3/2014 | Nagata et al. |
| 2002/0032386 | A1 | 3/2002 | Sackner et al. |
| 2002/0120207 | A1 | 8/2002 | Hoffman |
| 2003/0023178 | A1 | 1/2003 | Bischoff et al. |
| 2003/0045806 | A1 | 3/2003 | Brydon |
| 2003/0100843 | A1 | 5/2003 | Hoffman |
| 2003/0135127 | A1 | 7/2003 | Sackner et al. |
| 2003/0187341 | A1 | 10/2003 | Sackner et al. |
| 2004/0010202 | A1 | 1/2004 | Nakatani et al. |
| 2004/0133123 | A1 | 7/2004 | Leonhardt et al. |
| 2005/0228305 | A1 | 10/2005 | Nagata et al. |
| 2005/0240087 | A1 | 10/2005 | Keenan et al. |
| 2006/0100536 | A1 | 5/2006 | Nagai et al. |
| 2007/0282212 | A1 * | 12/2007 | Sierra ............... A61B 5/0205 600/529 |
| 2009/0012408 | A1 | 1/2009 | Nagata et al. |

FOREIGN PATENT DOCUMENTS

| | | |
|---|---|---|
| EP | 1095612 | 5/2001 |
| GB | 2016152 | 9/1979 |
| GB | 1596298 | 8/1981 |
| JP | 53-93681 | 8/1978 |
| JP | 53-126786 | 11/1978 |
| JP | 63-44011 U | 11/1988 |
| JP | 02-009771 | 1/1990 |
| JP | 2-9771 | 3/1990 |
| JP | 02-139608 U | 11/1990 |
| JP | 03-033605 | 2/1991 |
| JP | 3-33605 U | 4/1991 |
| JP | 03-116805 | 5/1991 |
| JP | 3-116805 | 12/1991 |
| JP | 4-51912 | 5/1992 |
| JP | 06-063031 | 3/1994 |
| JP | 06-197876 | 7/1994 |
| JP | 06-261871 | 9/1994 |
| JP | 06-319712 | 11/1994 |
| JP | 7-500748 | 1/1995 |
| JP | 7-75631 | 3/1995 |
| JP | 09-108188 | 4/1997 |
| JP | 09-271466 | 10/1997 |
| JP | 10-099299 | 4/1998 |
| JP | 10-211179 | 8/1998 |
| JP | 63-044011 U | 11/1998 |
| JP | 11-099299 | 4/1999 |
| JP | 11-128187 | 5/1999 |
| JP | 2600950 Y | 9/1999 |
| JP | 2600950 Y | 11/1999 |
| JP | 2002-035141 | 2/2002 |
| JP | 2002-053141 | 2/2002 |
| JP | 2002-159458 | 6/2002 |
| JP | 2002-325740 | 11/2002 |
| JP | 2003-530184 | 10/2003 |
| JP | 2004-049797 | 2/2004 |
| WO | WO 86/07248 | 12/1986 |
| WO | WO 93/08734 | 5/1993 |
| WO | WO 00/62667 | 10/2000 |
| WO | WO 01/78577 | 10/2001 |
| WO | WO 2004/004561 | 1/2004 |

OTHER PUBLICATIONS

International Search Report (Including English Translation) for International (PCT) Application No. PCT/JP2005/05393, mailed Jul. 12, 2005.
Written Opinion (Including English Translation) for International (PCT) Application No. PCT/JP2005/05393, mailed Jul. 12, 2005.
International Preliminary Report on Patentability (Including English Translation) for International (PCT) Application No. PCT/JP2005/05393, issued Oct. 18, 2006.
Supplementary European Search Report for corresponding European Patent Application No. 05721407.4, mailed Jul. 1, 2009.
Official Action for European Patent Application No. 05721407.4, mailed Oct. 7, 2009.
Official Action for Corresponding European Patent Application No. 05721407.4, dated Feb. 28, 2011, 4 pages.
Notification of Reasons for Refusal (with English translation) for corresponding Japanese Patent Application No. 2006-511320, dispatched Mar. 7, 2011, 4 pages.

(56) References Cited

OTHER PUBLICATIONS

Notification of Reasons for Refusal (including English translation) for corresponding Japanese Patent Application No. 2011-101110, mailed Mar. 4, 2013.
Notification of Reasons for Refusal (including English translation) for corresponding Japanese Patent Application No. 2011-101147, mailed Mar. 4, 2013.
Notification of Reasons for Refusal (including English translation) for corresponding Japanese Patent Application No. 2011-101165, mailed Mar. 4, 2013.
Official Action for U.S. Appl. No. 10/599,169, mailed Dec. 30, 2011.
Official Action for U.S. Appl. No. 10/599,169, mailed Mar. 7, 2012.
Official Action for U.S. Appl. No. 10/599,169, mailed Jul. 16, 2012.
Official Action for U.S. Appl. No. 10/599,169, mailed Dec. 18, 2013.
Official Action for U.S. Appl. No. 10/599,169, mailed Apr. 15, 2014.
Notice of Allowance for U.S. Appl. No. 10/599,169, mailed Feb. 23, 2015.
Supplementary European Search Report or European Application No. 05721410.8, dated Jul. 1, 2009.
European Office Action for European Application No. 05721410.8, dated Dec. 16, 2011.
European Search Report for European Application No. 11075027 mailed Dec. 8, 2011.
Partial European Search Report for European Application No. 11075027 mailed Mar. 31, 2011.
Japanese Official Action (including translation) for corresponding Japanese Application No. 2011-009046, mailed May 13, 2013.
Official Action for U.S. Appl. No. 10/599,173, mailed Mar. 26, 2008.
Official Action for U.S. Appl. No. 10/599,173, mailed Mar. 2, 2009.
Official Action for U.S. Appl. No. 10/599,173, mailed Sep. 29, 2009.
Official Action for U.S. Appl. No. 10/599,173, mailed Jan. 7, 2010.
Official Action for U.S. Appl. No. 10/599,173, mailed Sep. 13, 2010.
Notice of Allowance for U.S. Appl. No. 10/599,173, mailed Oct. 15, 2013.
Office Action for U.S. Appl. No. 14/682,260, mailed Feb. 10, 2016.
Notice of Allowance for U.S. Appl. No. 14/682,260, mailed Jun. 21, 2016.

* cited by examiner

RS AMPLITUDE VALUE(mV)

| Data No. | CHEST LEAD No.1 | No.2 | No.3 | No.4 | No.5 | No.6 | No.7 | No.8 |
|---|---|---|---|---|---|---|---|---|
| 1501 | 0.05 | 0.51 | 0.68 | 0.55 | 0.85 | 0.68 | 0.56 | 0.35 |
| 1502 | 0.09 | 0.58 | 0.72 | 0.54 | 0.81 | 0.59 | 0.48 | 0.21 |
| 1503 | 0.12 | 0.61 | 0.71 | 0.56 | 0.79 | 0.49 | 0.58 | 0.20 |
| 1504 | 0.08 | 0.61 | 0.65 | 0.54 | 0.78 | 0.42 | 0.49 | 0.58 |
| 1504 | 0.12 | 0.59 | 0.72 | 0.55 | 0.81 | 0.51 | 0.48 | 0.19 |
| 1530 | 0.11 | 0.59 | 0.71 | 0.66 | 0.79 | 0.54 | 0.48 | 0.18 |

TOTAL OF RS AMPLITUDE VALUES(mV)

| Data No. | CHEST LEAD No.1 | No.2 | No.3 | No.4 | No.5 | No.6 | No.7 | No.8 |
|---|---|---|---|---|---|---|---|---|
| 1501~1530 | 2.85 | 17.45 | 20.95 | 17.00 | 24.15 | 16.15 | 15.35 | 8.55 |

| | TOTAL OF RS AMPLITUDE VALUES(mV) | | |
|---|---|---|---|
| Data No. | CHEST LEAD SET 1 (LEADS No.1 THROUGH 6) | CHEST LEAD SET 2 (LEADS No.2 THROUGH 7) | CHEST LEAD SET 2 (LEADS No.3 THROUGH 8) |
| 1501~1530 | 98.55 | 111.05 | 102.15 |

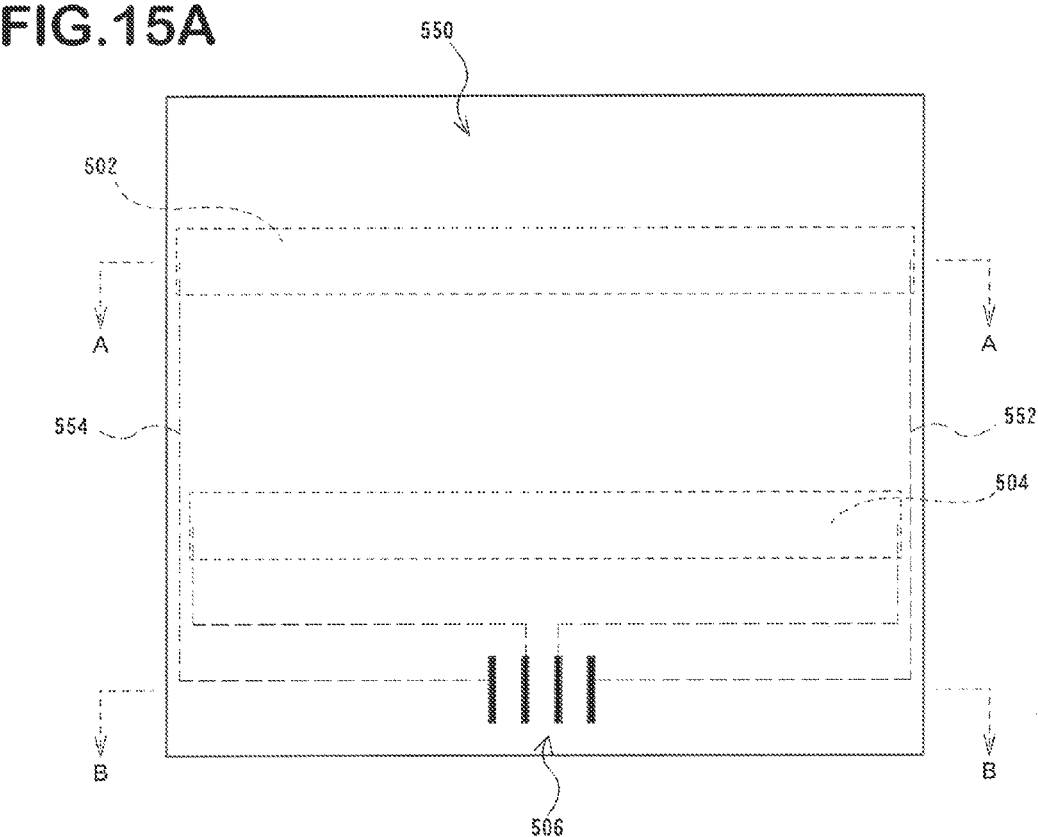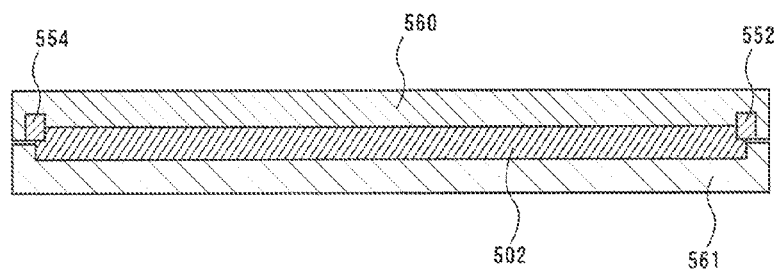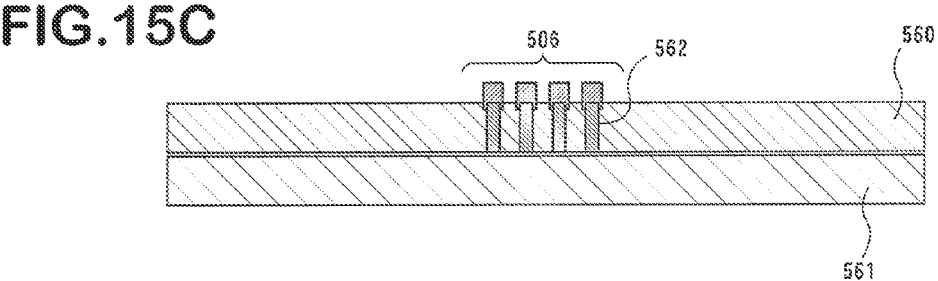

FIG.25A

| Data No. | RESISTANCE VALUE CYCLE (Hz) | R-WAVE HEIGHT CYCLE (Hz) | RESISTANCE VALUE AMPLITUDE (Ω) | R-WAVE HEIGHT AMPLITUDE (mV) |
|---|---|---|---|---|
| 1801 | 0.26 | 0.25 | 10.70 | 0.23 |
| 1802 | 0.28 | 0.24 | 10.80 | 0.23 |
| 1803 | 0.25 | 0.26 | 10.60 | 0.24 |
| AVERAGE | 0.26 | 0.25 | 10.70 | 0.23 |

FIG.25B

| Data No. | RESISTANCE VALUE AMPLITUDE (Ω) | R-WAVE HEIGHT AMPLITUDE (mV) | R-WAVE HEIGHT AMPLITUDE (Ω) (AFTER MEASUREMENT CONVERSION) |
|---|---|---|---|
| 1801-1803 AVERAGE | 10.70 | 0.23 | 10.81 |

FIG.26A

| Data No. | PEAK RESISTANCE VALUE (Ω) | PEAK POSITION (sec) | R-WAVE HEIGHT PEAK VALUE (mV) | BOTTOM RESISTANCE VALUE (Ω) | BOTTOM POSITION (sec) | R-WAVE HEIGHT BOTTOM VALUE (mV) | BOTTOM POSITION (sec) |
|---|---|---|---|---|---|---|---|
| 1501 | 19.2 | 2.502 | 0.70 | 7.9 | 4.402 | 0.51 | 4.395 |
| 1502 | 18.9 | 6.491 | 0.72 | 8.4 | 8.382 | 0.52 | 8.330 |
| 1503 | 19.1 | 10.380 | 0.69 | 8.2 | 12.520 | 0.49 | 12.460 |
| 1504 | 18.7 | 14.270 | 0.72 | 7.6 | 16.100 | 0.56 | 16.045 |
| 1543 | 18.9 | 168.200 | 0.78 | 8.1 | 170.150 | 0.52 | 170.148 |

FIG.26B

| Data No. | PEAK RESISTANCE VALUE (Ω) | PEAK POSITION (sec) | R-WAVE HEIGHT PEAK VALUE (mV) | BOTTOM RESISTANCE VALUE (Ω) | BOTTOM POSITION (sec) | R-WAVE HEIGHT BOTTOM VALUE (mV) | BOTTOM POSITION (sec) |
|---|---|---|---|---|---|---|---|
| 1501 | 19.2 | 2.502 | 0.70 | 7.9 | 4.402 | 0.51 | 4.395 |
| 1543 | 18.9 | 168.180 | 0.78 | 8.1 | 170.150 | 0.52 | 170.148 |
| AVERAGE | 19.1 | — | 0.75 | 7.9 | — | 0.51 | — |

FIG.26C

| Data No. | REFERENCE AMPLITUDE VALUE OF ELECTRIC RESISTANCE (Ω) (X) | REFERENCE AMPLITUDE VALUE OF R-WAVE HEIGHT (mV) (Y) | MEASUREMENT CONVERSION REFERENCE (X/Y) |
|---|---|---|---|
| 1501–1543 | 11.2 | 0.24 | 47 |

GARMENT FOR BIOINFORMATION MEASUREMENT HAVING ELECTRODE, BIOINFORMATION MEASUREMENT SYSTEM AND BIOINFORMATION MEASUREMENT DEVICE, AND DEVICE CONTROL METHOD

CROSS REFERENCE TO RELATED APPLICATIONS

This application is a divisional of U.S. patent application Ser. No. 10/599,169, filed Sep. 15, 2008, now U.S. Pat. No. 9,026,200, which is a national stage application under 35 U.S.C. 371 of PCT Application NO. PCT/JP2005/005393, having an international filing date of Mar. 24, 2005, which designated the United States, which PCT application claimed the benefit of Japanese Patent Application No. 2004-86110 (filed on Mar. 24, 2004), each of which are incorporated herein by reference in their entirety.

FIELD OF THE INVENTION

This invention relates to a garment for measuring biological information having electrodes, a biological information measurement system and a device for measuring biological information and a method of controlling thereof. Specifically, the present invention relates to measurement of biological information with accuracy even with differences in the constitution of an examinee, while having a simple structure.

BACKGROUND ART

Generally, the measurement of biological information, including cardiogram records, is carried out in a resting state of an examinee. For example, in the measurement of a cardiogram, the examinee lies on a bed for medical check-ups so as to put his/her back thereon and is in a resting state. The clinical technologist places EGC electrodes on chest, wrist, and ankle of the examinee respectively and then records a cardiogram with an electrocardiogram measuring device. Such measuring method of placing ECG electrodes, generally, induces large burden on the examinee because of displeasure resulting from electrode installation and some preparation time for measurement.

There is a technology that uses a T-shirt like clothes covering with a sutured conductive member for transmitting, for example, a biological electric signal to a recorder so as to suppress the burden given to the examinee and to acquire required biological information (for example, Patent document 1).

Patent document 1: Japanese laid-open publication No. 2002-159458 (FIG. 1)

According to the conventional art disclosed in the Patent document 1, it is advantageous that burden imposed on the examinee during the measurement of biological information can be suppressed.

However, the conventional art disclosed in the Patent document 1 just focused on suppressing the burden implied on the examinee. On the other hand, in the measurement of biological information, generally, where each examinee has unique body constitution of their own, it is necessary to consider the possibility of decreasing measurement sensitivity by the uniqueness. A much larger decrease of the sensitivity is expected if body movement become larger (during exercise, for example).

It is an object of the present invention to provide a garment for measuring biological information, a biological information measurement system and a method thereof capable of accurately measuring biological information even if there are differences in the unique body constitution of the examinee, while having a simple structure.

SUMMARY OF THE INVENTION

1) In accordance with characteristics of the present invention, there is provided a garment for measuring biological information formed of a nonconductive material having elasticity so as to fit on the upper body of an examinee, wherein chest lead electrodes, formed of a conductive material capable of acquiring a heart potential at vicinity of a chest part under a condition of less myoelectric influence regardless of variation of the heart position by forming the garment in a length so as to cover from the body surface around the fourth rib to the body surface around the sixth rib when the examinee wears the garment and capable of delivering the potential to a cardiogram analysis device, are arranged on the garment at least six positions from a position having a boarder with near presternal region of the examinee to vicinity of left chest lateral part.

With these features, the garment for measuring biological information can acquire a heart potential at vicinity of the chest part under a condition of less myoelectric influence regardless of variations of the heart position through the chest lead electrodes and deliver the heart potential to the cardiogram analysis device.

2) In accordance with characteristics of the present invention, there is provided a garment for measuring biological information formed of a nonconductive material having elasticity, wherein the garment having a length of more than 5 cm and less than 30 cm in a direction of the total length from vicinity of front center of the garment to vicinity of left side of the garment, and wherein chest lead electrodes, formed of a conductive material capable of acquiring a heart potential at vicinity of chest part when an examinee wears the garment, are arranged on the garment.

With these features, the garment for measuring biological information can acquire a heart potential at vicinity of chest part through the chest lead electrodes when an examinee (or a subject to be measured) wears the garment and deliver the heart potential to the cardiogram analysis device.

3) In accordance with characteristics of the present invention, there is provided a garment for measuring biological information formed of a nonconductive material, wherein chest lead electrodes, formed of a conductive material capable of acquiring a heart potential at vicinity of chest part under a condition of less myoelectric influence regardless of variation of the heart position of an examinee by forming the garment in a length so as to cover the body surface on the chest part when the examinee wears the garment and capable of delivering the potential to a cardiogram analysis device, are arranged on the garment between near presternal region of the examinee and vicinity of left chest lateral part.

With these features, the garment for measuring biological information can acquire a heart potential at a vicinity of chest part under a condition of less myoelectric influence regardless of variation of the heart position of an examinee through the chest lead electrodes and deliver the heart potential to the cardiogram analysis device.

4) In accordance with characteristics of the present invention, there is provided the garment for measuring biological information wherein the garment is a shirt worn on the upper body of the examinee, the shirt further comprising a four limb electrode having a dimension so as to at least cover one of the body surface of near collar bones of the examinee and the body surface of near the pelvis of the examinee and capable of acquiring an electric potential and capable of delivering the potential to the cardiogram analysis device.

With these features, the garment for measuring biological information can acquire an electric potential detectable at one of the body surfaces near the collar bones of the examinee and the body surface near the pelvis of the examinee via a four limb electrode and deliver the electric potential to the cardiogram analysis device.

5) In accordance with characteristics of the present invention, there is provided the garment for measuring biological information wherein the garment further comprises at least one chest electrode at a position from around a presternal region of the examinee to a position near a side of right chest and a position from near a side of the left chest to a position near the back, in addition to the chest lead electrodes.

With these features, the garment for measuring biological information acquires an electric potential generated by a living body through the at least one chest electrode in addition to the chest lead electrodes and delivers the electric potential to the cardiogram analysis device.

6) In accordance with characteristics of the present invention, there is provided a biological information measurement system comprising the garment according to any one of claims 1 through 5 and the cardiogram analysis device, wherein the cardiogram analysis device comprises:

electric potential information acquisition means acquiring information on electric potentials based on electric potentials delivered from a plurality of chest lead electrodes;

electric potential comparison means comparing amplitudes of the acquired electric potential information;

electric potential selection means selecting the chest lead electrodes detecting a larger amplitude as electric potential information to be based on an output of cardiogram in accordance with the comparison result of the electric potential comparison means; and cardiogram analysis output means outputting cardiogram data after analysis of the electric potential information detected by the selected chest lead electrodes.

With these features, the cardiogram analysis device can select electric potential information detected by the chest lead electrodes arranged at a position where the detection sensitivity is higher out of a plurality of electric potential information, for example, and outputs cardiogram data in accordance with the electric potential information.

9) In accordance with characteristics of the present invention, there is provided the biological information measurement system, wherein the cardiogram analysis output means further displays the position of the chest lead electrodes detecting the selected electric potential information correspondingly with a diagram of the examinee's body.

With these features, the user can visually and viscerally recognize the position of the chest lead electrodes detecting the selected electric potential information corresponding to the diagram.

10) In accordance with characteristics of the present invention, there is provided the biological information measuring garment on which a respiratory information measuring sensor, including a conductive member varying its electric resistance according to a variation of constitution of the examinee through breathing thereof under a turning-on-electricity state and capable of delivering electric information based on the variation of electric potential to a respiratory information analysis device, is arranged.

With these futures, the biological information measuring garment can acquire data for outputting respiratory information in addition to the data for outputting a cardiogram.

11) In accordance with characteristics of the present invention, there is provided the biological information measuring garment, wherein the respiratory information measuring sensor further disposed at least on one of a perimeter of the chest and a perimeter of the abdomen in the garment, and wherein electric resistance varies with expansion and contraction of one of the length and cross-section of the conductive member in response to the examinee's breathing.

With these features, the respiratory information measuring sensor can directly detect a physical change of the girth-of-the-chest length or the abdominal circumference length (beltline), for example, and the detection sensitivity caused by respiration can be stabilized.

12) In accordance with characteristics of the present invention, there is provided the biological information measuring garment, wherein for the respiratory information measuring sensor, electric influence under a turning-on-electricity state to the examinee is decreased by covering a surface of the conductive material facing the body surface of the examinee and an opposed surface thereof with nonconductive material.

With these features, the biological information measuring garment can decrease electric influence to the examinee when the measurement is carried out.

13) In accordance with characteristics of the present invention, there is provided the biological information measuring garment wherein the conductive member of the respiratory information measuring sensors is arranged at a plurality of positions at least including one of a position winding around the vicinity of chest of the examinee and a position winding around the vicinity of the abdomen of the examinee.

With these features, the biological information measuring garment can detect respiratory action of the examinee according to information detected at a plurality of positions including variation of a chest girth length and that of an abdominal circumference.

14) In accordance with characteristics of the present invention, there is provided a biological information measurement system comprising the garment according to one of claims 10 through 13 and the respiratory information analysis device, wherein the respiratory information analysis device comprises;

electric information acquisition means acquiring information on electricity delivered from the respiratory information measuring sensors;

electric information comparison means comparing a plurality of the acquired electric information;

electric information selection means selecting the respiratory information measuring sensors detecting a larger amplitude as electric potential information to be based on an output of respiratory information in accordance with the comparison result of the electric information comparison means;

respiratory information analysis means judging a variation cycle of the electric information detected with the respiratory information measuring sensors selected by the electric information selection means and analyzing respiratory information in accordance with the variation cycle; and respiratory information output means outputting respiratory information data in accordance with the analyzed respiratory information.

With these features, the respiratory information analysis device can select electric potential information detected by the chest lead electrodes arranged at a position where the detection sensitivity is higher from a plurality of electric potential information, for example, and outputs cardiogram data in accordance with the electric potential information.

17) In accordance with characteristics of the present invention, there is provided the respiratory information analysis system, the respiratory information analysis device, wherein the respiratory information analysis means further acquires information on a variation cycle of the electric information and R-wave height cycle information related on a variation cycle of R-wave height information of a cardiogram based on electric potentials delivered from the chest lead electrodes and selects cycle information of either one and analyzes respiratory information in accordance with the selected cycle information.

With these features, respiratory information analysis means can analyze respiratory action of the examinee according to a plurality of information including the variation cycle of the electric information and R-wave height cycle information.

18) In accordance with characteristics of the present invention, there is provided the respiratory information analysis system, wherein the respiratory information analysis means further acquires information on amplitude of the electric information and R-wave height amplitude information related to amplitude of the R-wave height information and selects one of the electric information and the R-wave height information in accordance with comparison of the electric information and the R-wave height information and analyzes respiratory information in accordance with the selected cycle information.

With these features, the respiratory information analysis means can select either one of the electric information and the R-wave height information which has a higher detection sensitivity, and can analyze respiratory action of the examinee according to its cycle information.

19) In accordance with characteristics of the present invention, there is provided the respiratory information analysis system, wherein further the respiratory information analysis means display one of a position of the chest lead electrodes and a position of the respiratory information measuring sensor detecting the selected information correspondingly with one of a diagram of the biological information measuring garment and a diagram of the examinee's body.

With these features, the user can visually and viscerally recognize the position of the chest lead electrodes detecting the selected electric potential information corresponding to the diagram.

Other features, objects usage and advantages of the present invention will be more apparent to those skilled in the art in consideration of the accompanying drawings.

BRIEF DESCRIPTION OF THE DRAWINGS

FIGS. 12A, 12B and 12C are views showing data record of RS amplitude calculated by a CPU in the second embodiment;

FIG. 15A is a partial view of the shirt for measuring biological information according to the third embodiment, FIG. 15B is a partial sectional view taken on a direction A-A of FIG. 15A, and FIG. 15C is a partial sectional view taken on a direction B-B of FIG. 15A;

FIGS. 25A and 25B are views showing data record of a resistance cycle, a resistance amplitude, an R-wave height cycle, an R-wave height amplitude and the like calculated by a CPU in the fourth embodiment;

FIGS. 26A, 26B and 26C are views showing data record of resistance values (peak values, bottom values etc.) and an R-wave height (peak values, bottom values etc.) and the like calculated by a CPU in the fourth embodiment.

DETAILED DESCRIPTION OF DESIRED EMBODIMENTS

Figure 1:
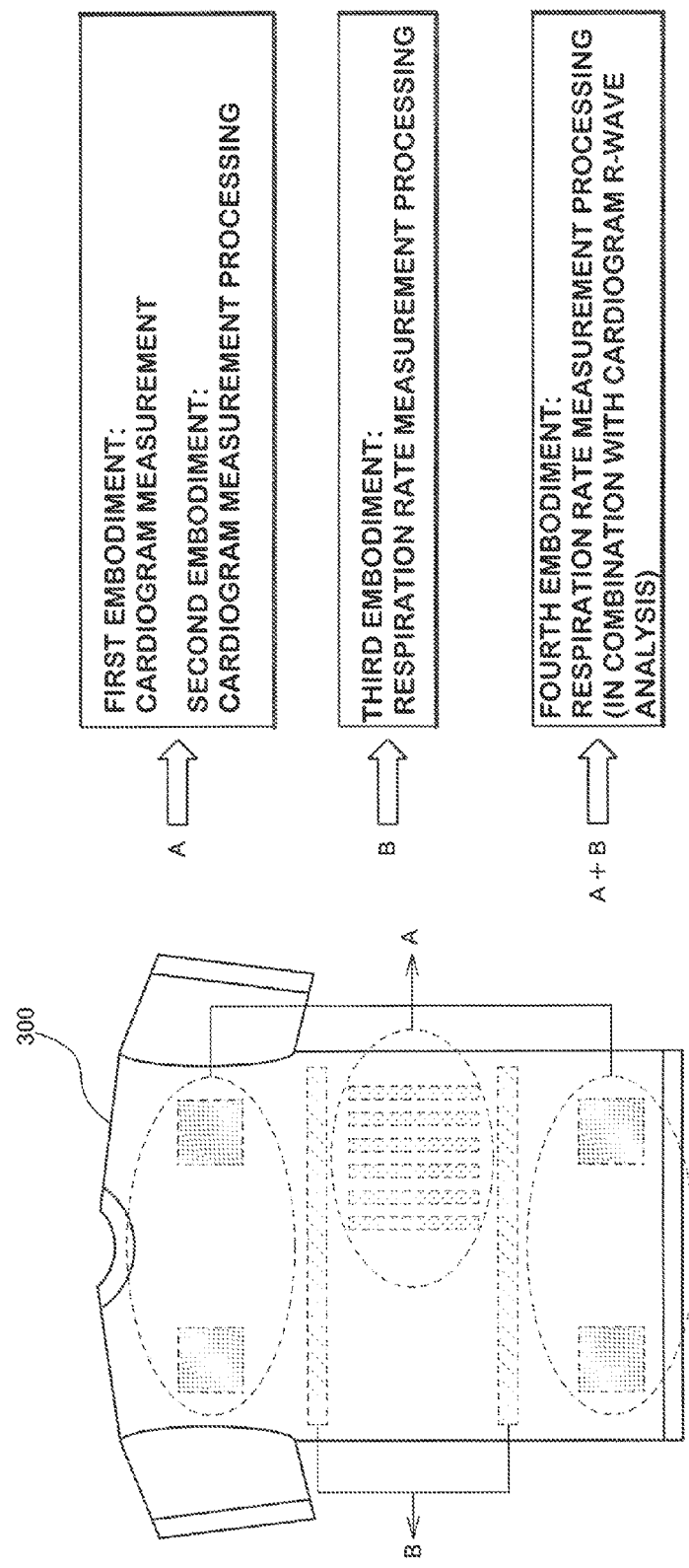
FIG. 1 is a diagram illustrating an overview of each of embodiments.

Embodiments of the "garment for measuring biological information" and the "biological information measurement system" according to the present invention will be described. FIG. 1 is a diagram illustrating an overview of each of embodiments.

A biological information measuring shirt, as an embodiment of the "garment for measuring biological information" which is put on the upper body of an examinee, comprises electrodes (A) placed on the chest region and the four limbs and sensors (B) disposed on a beltline and a abdominal line. In a cardiogram measurement according to the first embodiment and a cardiogram measurement process according to the second embodiment, information delivered from the electrodes (A) are utilized. On the other hand, information delivered from the sensor (B) is used in a respiration rate measurement according to the third embodiment. Information delivered from both the electrodes (A) and the sensors (B) is utilized in respiration rate measurement processing (in combination with cardiogram R-wave analysis).

Hereinafter, correspondence among the biological information measuring shirt, hardware structure included in the system and claimed wording and description in these embodiments will be clarified, and then a detailed description of the embodiments will be described.

TABLE OF CONTENTS

Figure 2:
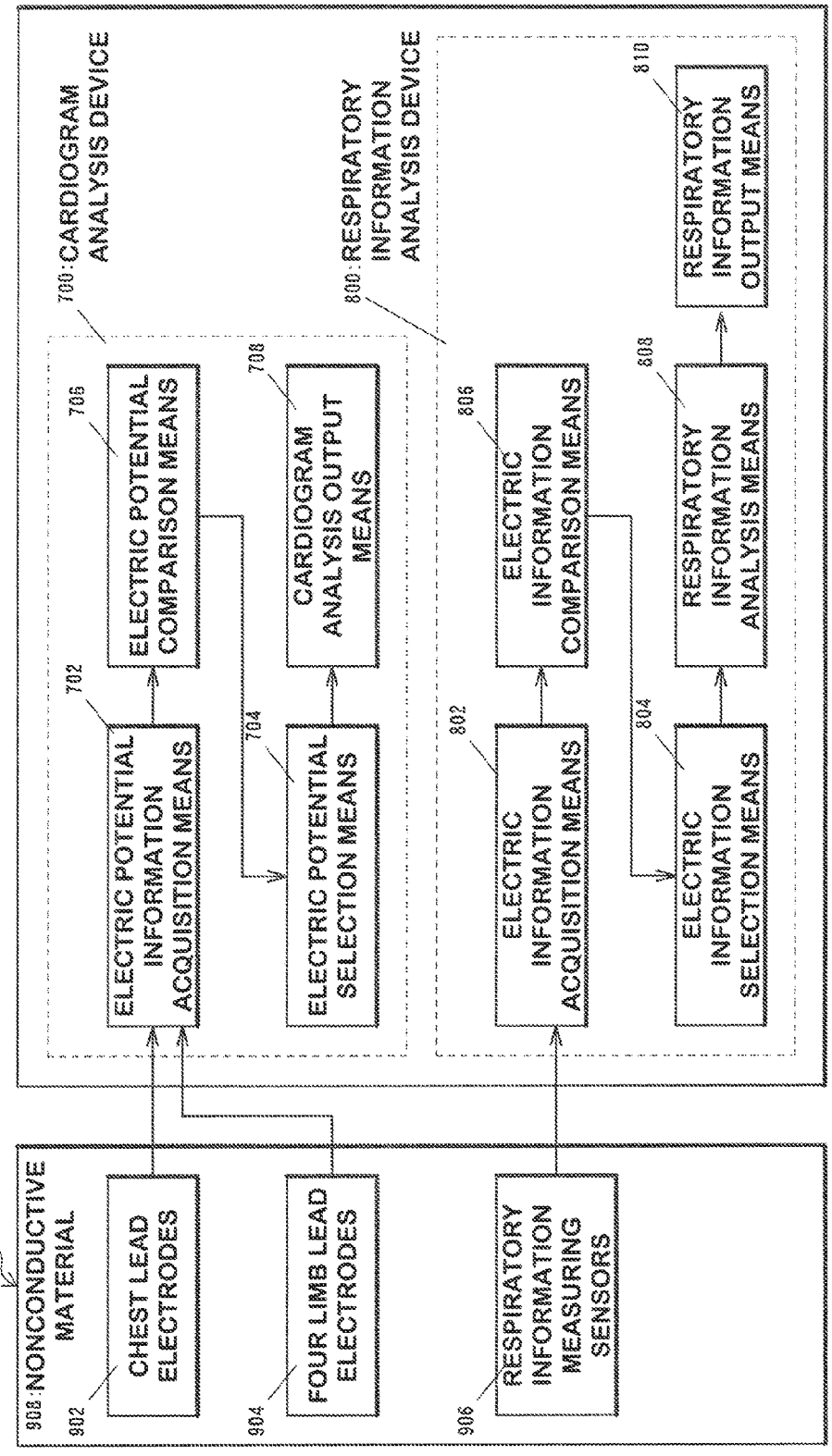
FIG. 2 is a functional block diagram of biological information measurement system according to an embodiment.

1. Structure of the biological information measuring shirt and that of the system
2. Correspondence between claimed wording and supported element of the embodiments
3. First embodiment (cardiogram measurement)
4. Second embodiment (cardiogram measurement processing)
5. Third embodiment (respiration rate measurement processing)
6. Fourth embodiment (respiration rate measurement processing (in combination with cardiogram R-wave analysis))
7. Other embodiments and others 1. Structure of the Biological Information Measuring Shirt and that of the System FIG. 2 is a functional block diagram of a biological information measurement system 1000 as "biological information measurement system" according to the present invention. The biological information measurement system 1000 comprises a garment for biological information measurement 900, a cardiogram analysis device 700 and a respiratory information analysis device 800.

Also, the garment 900 is made of a nonconductive material 908 and comprises chest lead electrodes 902, four limb lead electrodes 904 and respiratory information measuring sensors 906. The cardiogram analysis device 700 comprises electric potential information acquisition means 702 acquiring information on electric potentials from the chest lead electrodes 902 and(or) four limb lead electrodes 904, electric potential comparison means 706 comparing a plurality of the electric potential information, electric potential selection means 704 selecting the chest lead electrodes in accordance with the electric potential information and cardiogram analysis output means 708 outputting cardiogram data after analysis of the electric potential information.

The respiratory information analysis device 800 comprises electric information acquisition means 802 acquiring information on electricity from the respiratory information measuring sensors 906, electric information comparison means 806 comparing a plurality of the electric information, electric information selection means 804 selecting the respiratory information measuring sensors 906 in accordance with the electric information, respiratory information analysis means 808 analyzing respiration data in accordance with information on respiration and respiratory information output means 810 outputting respiratory information data in accordance with the respiratory information.

Figure 3:
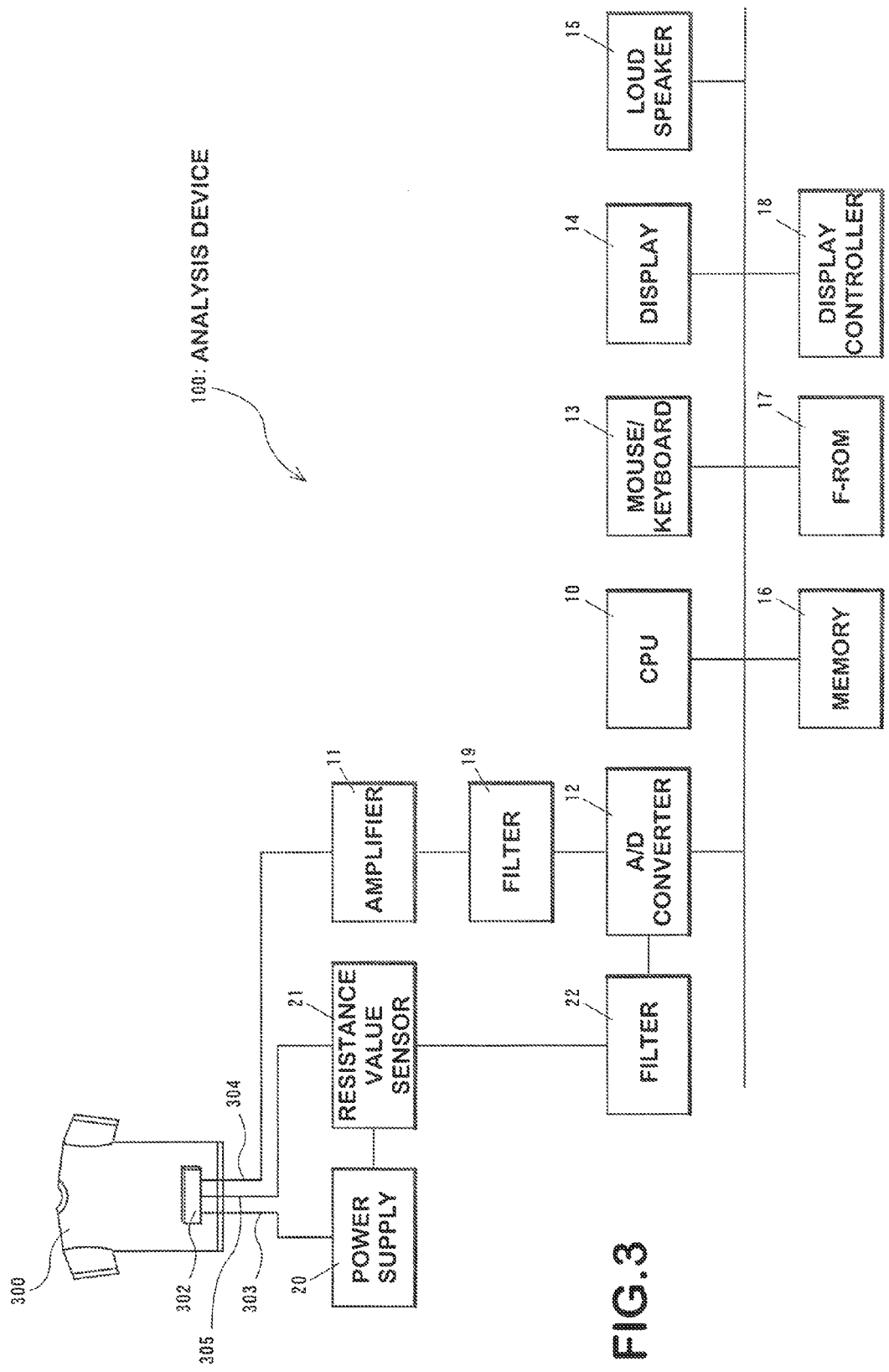
FIG. 3 is a diagram illustrating an overall configuration of the biological information measurement system according to the first embodiment.

FIG. 3 is a diagram illustrating a hardware structure of the cardiogram analysis device 700 and (or) the respiratory information analysis device 800 in the biological information measurement system 1000 using a CPU. The description is made for an embodiment where functions of the cardiogram analysis device 700 and the respiratory information analysis device 800 are carried out with one device (an analysis device 100). Such analysis device 100 may perform one of the functions of the cardiogram analysis device 700 and the respiratory information analysis device 800.

The analysis device 100 comprises a CPU 10, an amplifier 11 for amplification, a filter 19, an A/D converter 12, a mouse/keyboard 13, a display 14 (display device), a loud speaker 15, a memory 16, a Flash-ROM 17 (a rewritable read only memory by which data stored therein can electrically erasable, such as flash memory, hereinafter referred to as F-ROM 17), a display controller 18, a power supply 20, a resistance value sensor 21 and a filter 22. The analysis device 100 is connected to a connector 320 via a power cable 304 and (or) a power cable 303. The connector 302 is connected to a biological information measurement shirt 300.

The connector 302 delivers to the amplifier 11 the heart's electricity of an examinee obtained via electrodes described later. The amplifier 11 amplifies information on the heart's electricity delivered via the connector 302. The filter 19 removes noise component (noise) from signal output from the amplifier 11. The A/D converter 12 converts the information on the electricity (analog data) to digital data.

The power supply 20 turns a predetermined part of the shirt 300 on electricity via the power cable 303 and the connector 302. The resistance value sensor 21 measures electric current values flow through predetermined parts via a resistance measurement code 305 when a certain voltage is applied via the power supply 20 and the like, and acquires resistance values at predetermined parts in accordance with the measured current values. The filter 22 removes noise components (noise) on information from the resistance value sensor 21. The A/D converter 12 converts resistance value (analog data) to digital data.

The CPU 10 entirely controls the analysis device 100 besides performing a cardiogram measurement processing, a respiration rate measurement processing, and so on. The F-ROM 17 records a program for controlling the analysis device 100. The memory 16 provides a work area and so on for the CPU 10. Operating information generated through the operation of the mouse/keyboard 13 or the display controller 18 is input into the CPU 10, and the image information and the audio information generated by the CPU 10 are respectively output to the display 14 and the speaker 15.

In the embodiments, dedicated software is used as an exemplary software for the analysis device 100 to perform cardiogram measurement processing and respiration rate measurement processing.

In the embodiments, the exemplary operating system (OS) used for the analysis device 100 is one of Microsoft Windows (Registered Trademark) XP, NT, 2000, 98SE, ME, CE and so on. Although, the program used in this embodiment cooperates with the OS in order to achieve each of the functions, these functions may also be achieved by a control program itself.

"Cardiogram" described in the embodiments is obtained by measuring a difference in electric potentials for two points of the body of an examinee. It is, therefore, the term "measurement of a cardiogram" includes a concept of measuring electric potentials, etc.

Each of the functions and variations of the biological information measurement shirt 300 will be described independently for the purpose of clarity throughout the first to the fourth embodiments herein. As a result, shirt 300 may also be achieved by having just one of the functions described throughout the first to the fourth embodiments or be achieved by having combination of the function(s) with each of the structures.

The shirt 300 will be described as a biological information measurement shirt 301, and so on, a biological information measurement shirt 400, and so forth, a biological information measurement shirt 500, and so on and a biological information measurement shirt 600, and so forth, respectively the first, the second, the third and the fourth embodiments.

Further, it is apparent to the person ordinary skilled in the art to make modification to the size, material, the way of weave, manufacturing process, and so on because the biological information measurement shirts are just examples thereof.

2. Correspondence Between Claimed Wording and Supported Elements of Embodiments Correspondence between claimed wording and supported embodiments is as follows. But, the term "corresponding embodiment(s)" described below shows one configuration (or partial configuration) out of functions represented by the terms defined in the claims.

The term "garment for measuring biological Information" corresponds to the biological information measurement shirt 300 (FIG. 1), and the like. The term "cardiogram analysis device" corresponds to the analysis device 100 (FIG. 3). Also, the term "conductive material" is a general term including a material having conductivity, and it corresponds to electrodes for chest region formed by conductive fabric (or formed by conductive yarn) and electrodes for four limbs. Further the term "chest lead electrode" corresponds to the electrodes for chest region 353, 354, 355, 356, 357, 358 (FIG. 4), and so on. The term "four limbs lead electrode" corresponds to the electrodes for the four limbs 351, 352, 361, 362 (FIG. 4), and so on.

Figure 10:
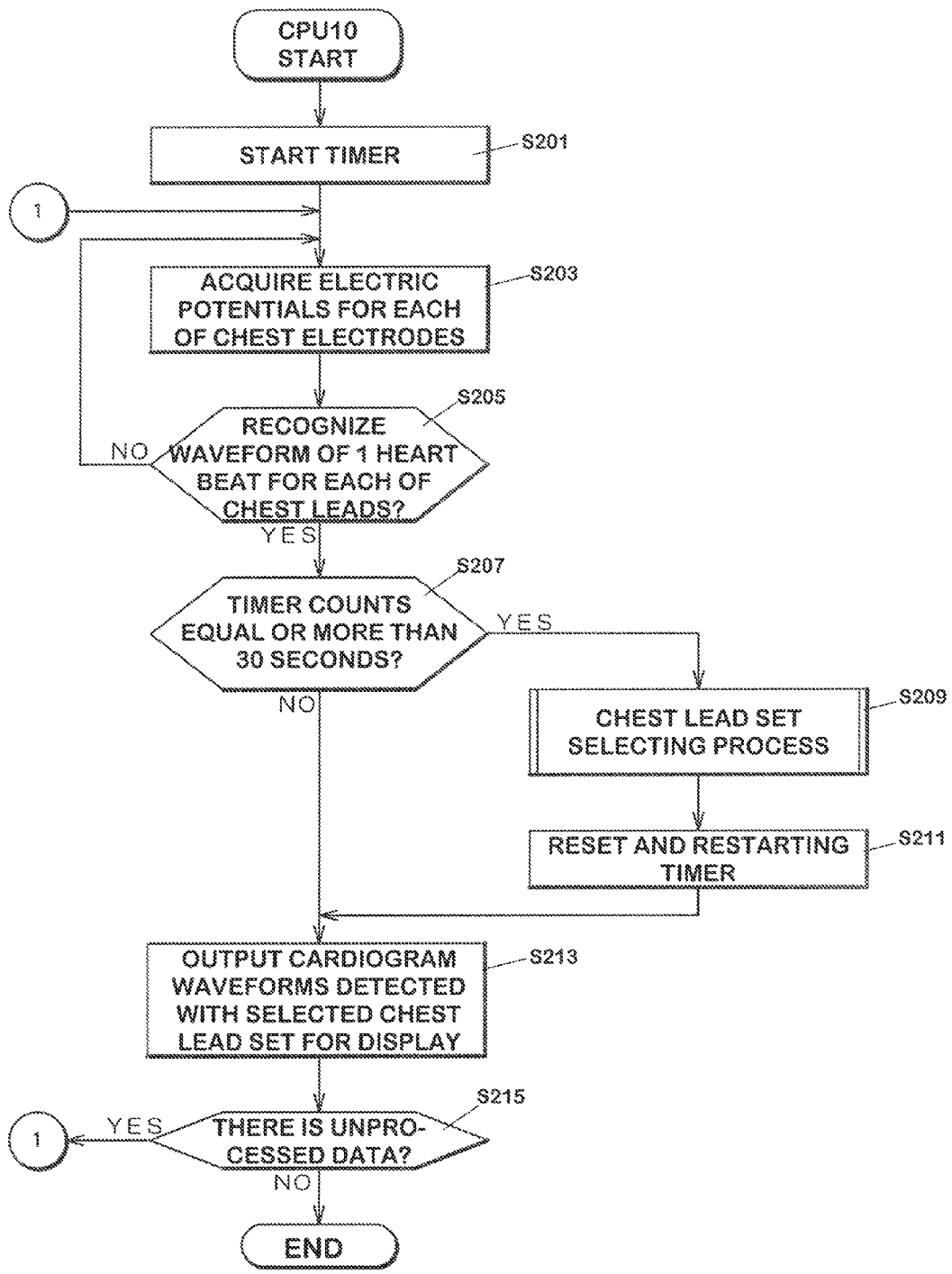
FIG. 10 is a flowchart showing process for cardiogram measurement according to the second embodiment.
Figure 11:
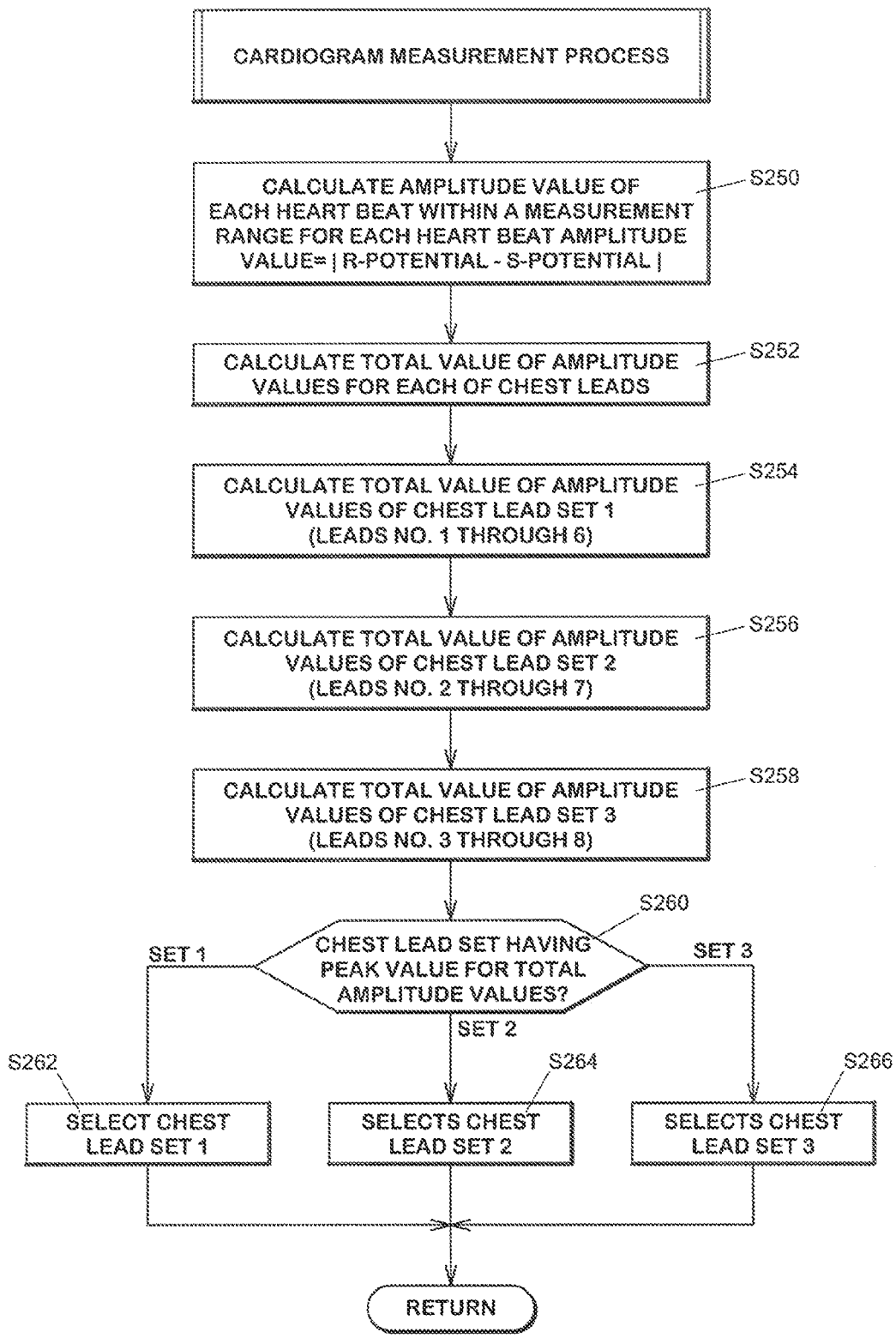
FIG. 11 is a flowchart showing process for cardiogram measurement according to the second embodiment.

The term "electric potential information" corresponds to information obtained during the process performed at step S203 shown in FIG. 10. Also, the term "electric potential information acquisition means" has a function of acquiring information on electric potential and corresponds to a CPU 10 of the analysis device 100 performing steps S203 and (or) 205 shown in FIG. 10, for example. Further, the term "electric potential information comparison means" has a function of comparing amplitude of electric potential information and corresponds to, for example, the CPU 10 performing step S260 as shown in FIG. 11. Still further the term "electric potential information selection means" has a function of selecting electric potential information and corresponds to the CPU 10 performing one of the steps S262 and S264 shown in FIG. 11, for example.

The term "cardiogram data" corresponds to fundamental data for cardiogram waveform output for display at step S213 shown in FIG. 10. Also, the term "cardiogram analysis output means" has a function of carrying out analysis of electric potential information and outputting for display and corresponds to, for example, the CPU 10 performing step S213 shown in FIG. 10.

The term "conductive member" is a general term representing a member including a material having conductivity (or combination of materials including a conductive material), and it corresponds to a chest respiratory information sensor 502 or an abdominal respiratory information sensor 504 (FIG. 15). The term "electrical information" is information based on a variation of electric resistance, and it corresponds to the resistance value data acquired at step S402 shown in FIG. 22 performed by the CPU 10. Further, the term "respiratory information analysis device" corresponds to analysis device 100. Still further, the term "respiratory information measuring sensor" corresponds to the chest respiratory information sensor 502 or the abdominal respiratory information sensor 504 (FIG. 15) and the like.

Figure 21:
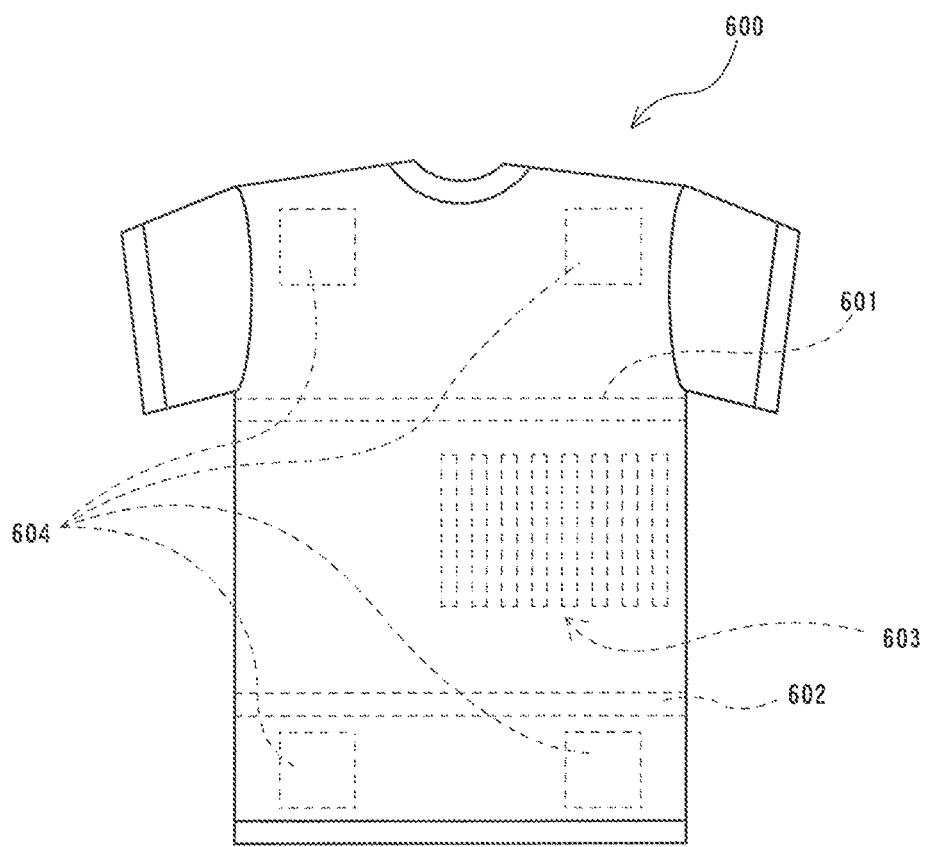
FIG. 21 is an overall view of a shirt for measuring biological information according to the fourth embodiment.
Figure 22:
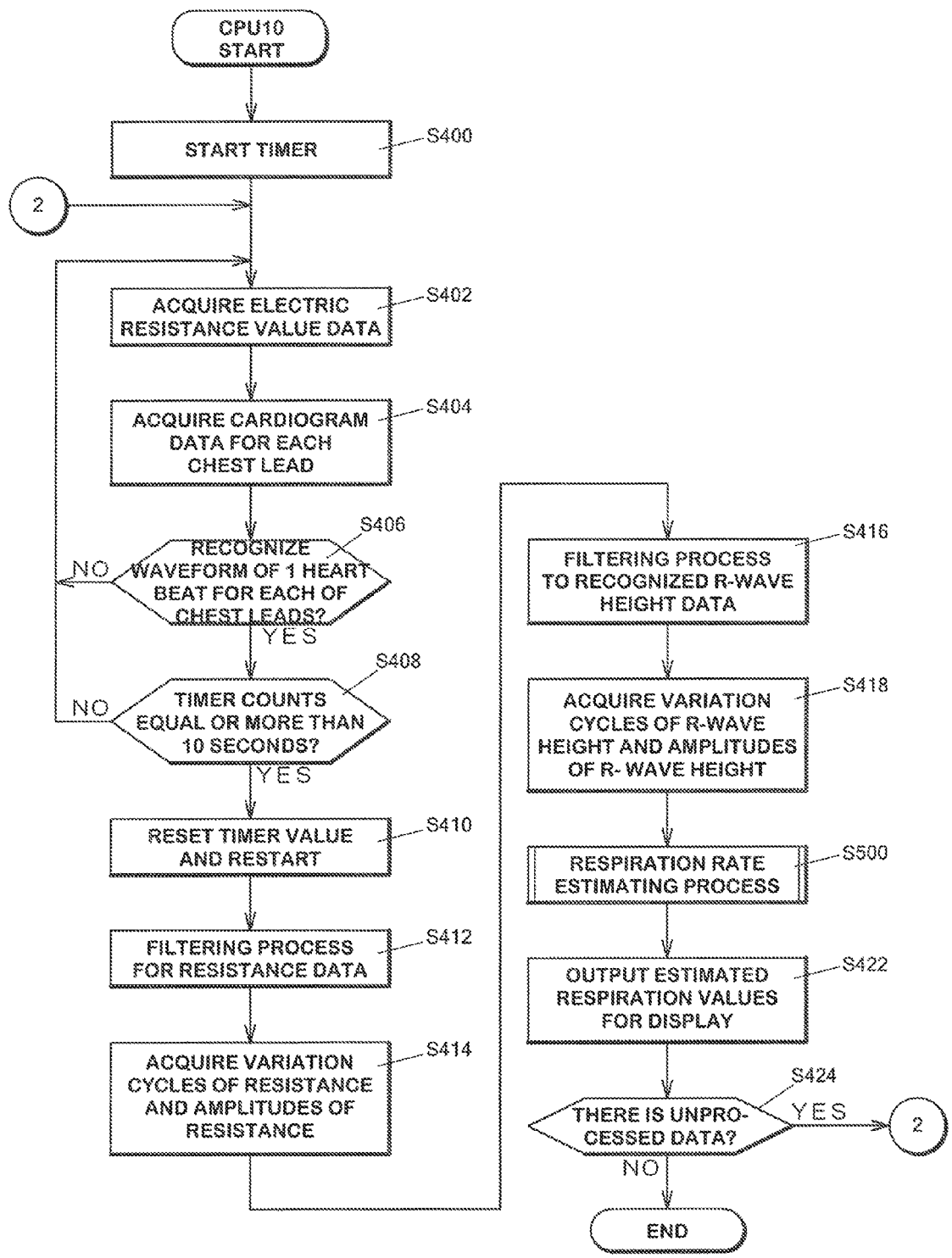
FIG. 22 is a flow chart for processing measurement of respiration rates according to the fourth embodiment.

Yet further, the term "electric information acquisition means" has a function of acquiring electric information and corresponds to, for example, the CPU 10 performing step S402 shown in FIG. 22. Also, the term "electric information comparison means" has a function of comparing a plurality of the amplitudes of electric information and corresponds to a CPU 10 performing a comparison between the amplitude of resistance value data (or a total value of the amplitude) originated by a chest respiratory information sensor 601 (FIG. 21) and that originated by an abdominal respiratory information sensor 602 which is done subject to step S500 in the fourth embodiment shown in FIG. 22. Further, the term "electric information selection means" has a function of selecting electric information and corresponds to a CPU 10 performing a process of selecting one of resistance data originated by the chest respiratory information sensor 601 and the abdominal respiratory information sensor 602 based on the comparison by the "electric information comparison means".

The term "respiratory information analysis means" has a function of analyzing information on respiration in accordance with a variation cycle of electric information and corresponds to the CPU 10 calculating an estimated respiration value at step S422 shown in FIG. 22. The term "respiration data" corresponds to data representing respiration rate calculated at step S422. The term "respiratory information output means" has a function of outputting respiratory information data corresponds to the CPU 10 performing a process of displaying on a display an estimated respiration value at step S422 shown in FIG. 22.

The term "electric cycle information" corresponds to information on a variation cycle of resistance acquired by the CPU 10 at step S414 shown in FIG. 22 (information of "resistance value cycle" shown in FIG. 25A). Also, the term "R-wave height information" corresponds to information on an R-wave height (R-potential) identified in a process carried out at step S406 shown in FIG. 22. Further, the term "R-wave height cycle information" corresponds to information on a variation cycle of an R-wave height acquired by the CPU10 acquired in a process carried out at step 414. (Information of "resistance amplitude" shown in FIG. 25A). Still further, the term "R-wave height information" corresponds to information on amplitude of an R-wave acquired by the CPU10 in a process carried out at step 414. (information of "R-wave height amplitude" shown in FIG. 25A).

3. First Embodiment

Cardiogram Measurement

3-1. Biological Information Measurement Shirt

Figure 4A:
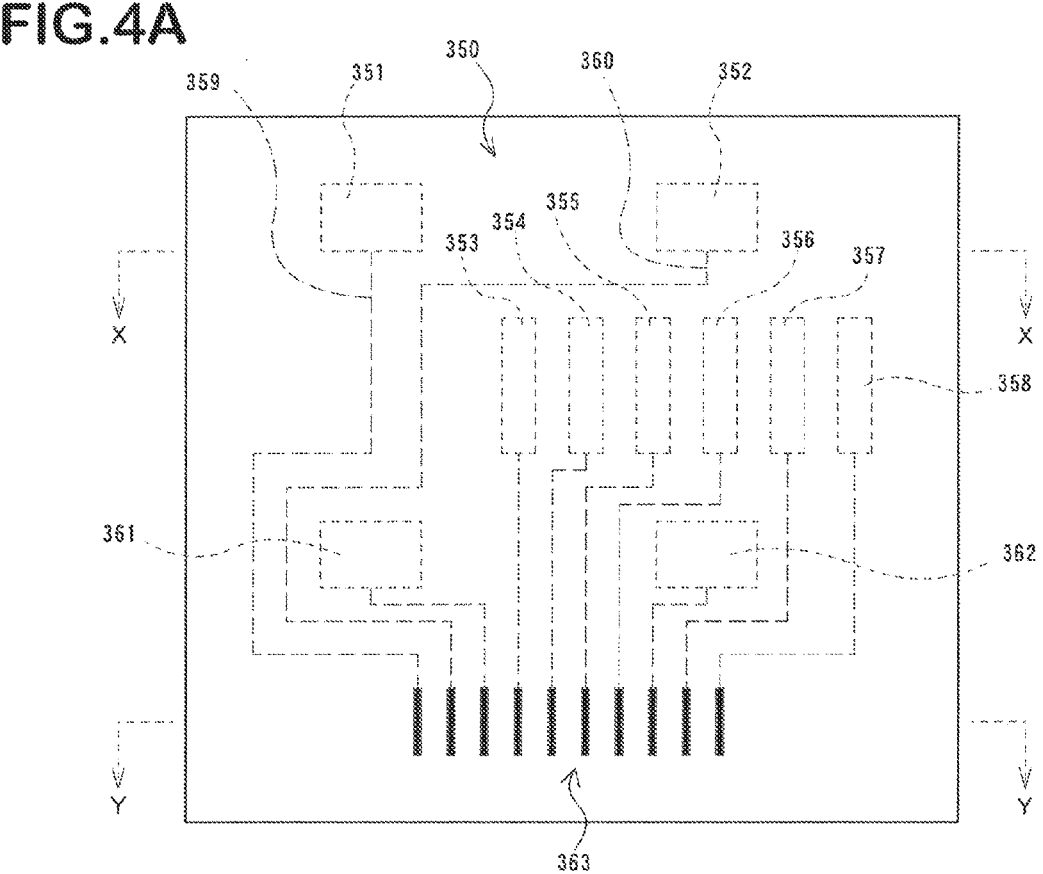
FIG. 4A is a partial view of a shirt for measuring biological information according to the first embodiment.

A biological information measurement shirt 300 according to the first embodiment will be described with reference to FIGS. 4 and 5. FIG. 4A shows the front body (chest side) of the biological information measurement shirt 301 in the manufacturing process thereof before cutting. The biological information measurement shirt 301 consists of a shirt part 350 formed of an elastic fabric having nonconductive property and an electrode part described later. Examples of such elastic fabrics having nonconductive property are below.

Elastic chemical fabrics such as polyurethane

Natural fabrics such as cotton, linen, silk and wool and the like having elasticity by knitting plain knitting or Jersey stitch, rubber knitting or rib knitting, or fraise knitting Elastic fabric such as rubber into which fabrics are weaved Combination of the above mentioned fabrics The shirt part 350 according to the embodiment uses a Fabric formed of a cotton yarn knitted with rib-knitting. It is preferred to use means for fit each of electrodes described later on the body surface of the examinee when the shirt part with no elasticity is used. In order to fit each of the electrodes on the body surface of the examinee, a low irritant acrylic adhesive for example, may be applied on each of the electrodes which fit on the body surface.

In the biological information measurement shirt 301, chest electrodes and four limbs electrodes formed of conductive material are knitted therein. In this embodiment, a conductive fabric knitted on the back side of the shirt part 350 (the side that contacts with the body surface) shown in FIG. 4A is used as examples of the chest electrodes and four limbs electrodes. Here, a fabric adhering (through chemical binding, for example) metal particles (silver particles, copper particles, or copper sulfide particles, for examples) there on (for example Thunderron (registered Trademark) manufactured by Nihon Sanmo Dyeing Co., Ltd.) is used in the embodiments.

Chest electrodes comprise a total of six electrodes (a longitudinally formed strip shaped one) such as a chest electrode 353, a chest electrode 354, a chest electrode 355, a chest electrode 356, a chest electrode 357 and a chest electrode 358. Four limbs electrodes comprise a total of four electrodes for four limb lead electrodes such as a four limb electrode 351, a four limb electrode 362, a four limb electrode 361 and a four limb electrode 354.

Each of the electrodes connected to a connector assembly 364 as a terminal assembly of each of the wire connections. In the embodiments, a conductive fabric similar to the chest electrodes and (or) the four limb electrodes is used as an example of a wire connection and connector assembly 363. The four limb electrodes 351 are connected to the connector assembly 363 with a wire connection 359. The four limb electrodes 352 are connected to the connector assembly 363 with a wire connection 360. Similarly, other electrodes are connected to the connector assembly 363 with the wire connections. The four limb electrode 361 is used as an intermediate electrode as appropriate.

The following are possible dimensions the shirt part 350 and other parts shown in FIG. 4A. These dimensions are just examples, variations can be made by age, gender and other parameter(s).

Shirt part 350: longitudinal direction (body length, the following -- the same) approx. 60 cm×approx. 50 cm wide Four limb electrodes 351, 352, 361, 362: longitudinal direction approx. 3 cm×approx. 6 cm wide Position for upper side of four limb electrode 351 (352): approx. 4.5 cm from the upper side of the shirt part 350

Position for left side of four limb electrode 351 (361): approx. 10.5 cm from the left side of the shirt part 350

Position for right side of four limb electrode 352 (362): approx. 10.5 cm from the right side of the shirt part 350

Position for lower side of four limb electrode 361 (362): approx. 18 cm from the lower side of the shirt part 350

Distance between four limb electrodes 351-352 (361-362): approx. 18 cm Chest electrodes 353-358: longitudinally approx. 12×approx. 3 cm wide, approx. 1 cm in respective space (desired dimensions within a range, longitudinal direction for example, approx. 5 cm or 8 cm or 10 cm in lower limit, approx. 30 cm or 20 cm or 15 cm in upper limit may also be used)

Position of left side of chest electrode 358: approx. 2 cm from the right side of the shirt part 350

Position of lower side of connector assembly 363: approx. 6 cm from the lower side of the shirt 350

Connecting wires (connecting wires 359, 360 and the like): approx 6 cm wide respectively Position of each connecting wires (the connecting wires 359, 360 and the line, for example) approx. 6 cm wide respectively The connector assembly 363: approx. 3 cm wide for each connecting wire Manufacturing process of the biological information measurement shirt 301 is sequentially carried out under the following steps: (1) knitting the chest electrodes and the four limb electrodes into the shirt part; (2) forming the front part by cutting a resultant of the step (1); (3) forming the back side, sleeves and collar and other details; (4) sewing each of the front side, the back side, the sleeves and the collar of the back side. Conventional technologies to a person skilled in the art such as knitting by hand (or) using a computer controlled sewing machine may be employed for the step "(1) knitting the chest electrodes and the four limb electrodes into the shirt part" in the manufacturing process.

Figure 4B:
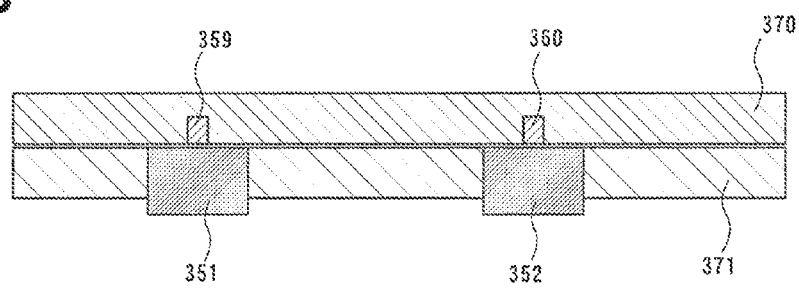
FIG. 4B is a partial sectional view taken on a direction X-X of FIG. 4A.

FIG. 4B is a partial sectional view taken on a direction X-X of FIG. 4A. In the embodiments, the biological information measurement shirt 301 is formed as a double cloth shirt, for example. The shirt part 350 is formed as a single cloth fabricated by piling a woven part 370 of a nonconductive material and a woven part 371 thereof. The four limb electrode 351 and the four limb electrode 352 are knitted into a part of the woven part 371 instead of nonconductive material. The method of forming the four limb electrode 351 and the four limb electrode 352 and others on the shirt 350 is not limited to that shown in FIG. 4. Other method, for example, a method of cutting a part of the woven part 371 and fix the four limb electrode 351 and the four limb electrode 352 to the cut part with any adhesion member may be used. Or the four limb electrode 351 and the four limb electrode 352 may be knitted into the woven part 371 with another yarn.

The connecting wires 359, 360 are respectively knitted into the four limb electrodes 351 and the four limb electrodes 352. It is, therefore, both the connecting wires 359, 360 are knitted at positions so as to be sandwiched between the woven part 370 and the woven part 371. It is preferred that the examinee can not touch the connecting wires to avoid the influence to cardiogram measurement. Similarly, other chest electrodes and four limb electrodes and the connecting wires connected thereto are formed in a double cloth.

Figure 4C:
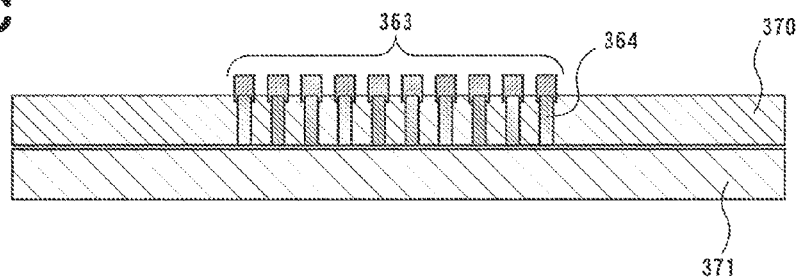
FIG. 4C is a sectional view taken on a direction Y-Y of FIG. 4A.

FIG. 4C is a sectional view taken on a direction Y-Y of FIG. 4A. A part contacting with the connector assembly 363 of the woven part 370 is defined as a terminal part of the connecting wiring in that fabric. The connector assembly 363 is knitted so that it contacts with the woven part 370. The connecting wires wiring from each of the electrodes are knitted at positions so as to be sandwiched between the woven part 370 and the woven part 371 (see FIG. 4B), they are electrically connectable to the connector assembly 363 by knitting a part of the woven part 370 at a part connecting with the connector assembly 363.

By employing the above described structure for the shirt 350, biological current obtained from each of the chest electrodes and each of the four limb electrodes is electrically conveyed through the connecting wires connected to the electrodes to the connector assembly 363.

3-2. Biological Information Measurement Shirt 301 (During Wear)

Figure 5A:
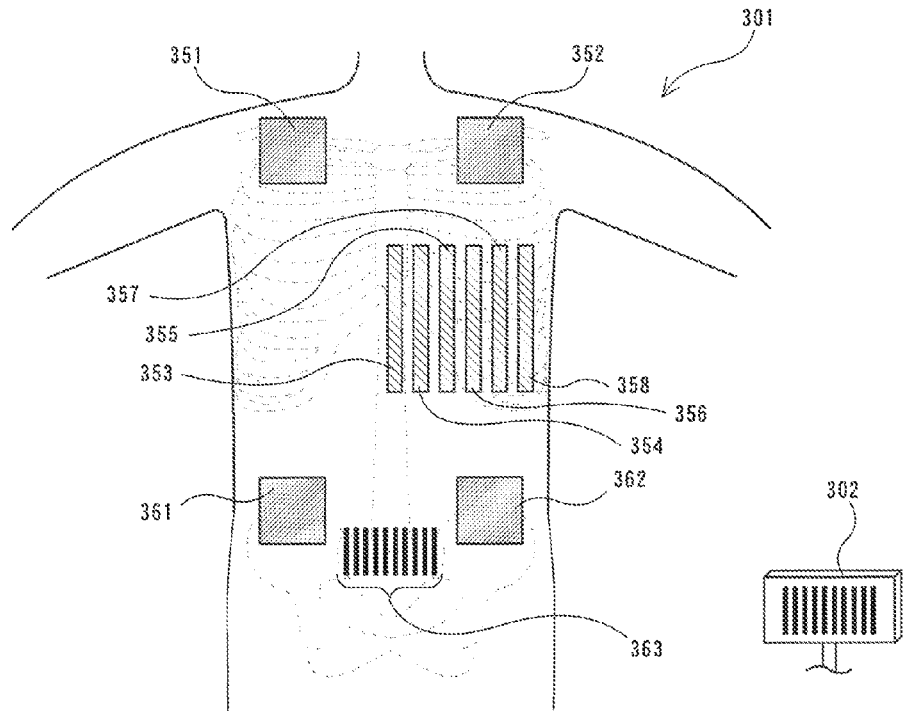
FIG. 5A is a diagram showing correspondence between the shirt for measuring biological information and the constitution of an examinee.

FIG. 5A is a diagram showing correspondence between the shirt for measuring biological information and the constitution of an examinee. In this diagram, the biological information measurement shirt 301 is not shown and only the correspondence between each of the electrodes and the constitution of the examinee is illustrated for simplicity. When the examinee wears the shirt 301, the four limb electrodes 351 and 352 are arranged at positions so that the electrodes cover the body surface (skin surface) other than around the clavicle of the examinee. At that time, the four limb electrodes 361 and 362 are assigned to positions so that they cover about the pelvis of the examinee. Also, during the use of the shirt, the chest electrodes 353~358 cover from the body surface (around lower part of left side of the body) of a presternal region around the left thorax of an examinee for a perpendicular direction of the body axis (a direction perpendicular to the length of the shirt) and the electrodes are assigned so as to cover from the body surface around the fourth rib to that around the sixth rib (or around the seventh rib, or around eighth rib, or the lower border of the ribs).

The arrangement and assignment of the chest electrode and the four limb electrodes are just examples, variation and adjustment can be carried out with known methodology. For example, the chest electrodes may also be arranged at positions so as to cover the body surface around the ribs on the anterior surface of the heart. But it is desirable to arrange the chest electrodes and the four limb electrodes so that they receive not much influence of noises other than electric potentials such as myoelectrical potentials.

The connector assembly 363 has 10 connecting wire ends so as to electrically connect with each of the electrodes. The connector 302 has 10 electric terminals for electrically connecting these 10 connecting wire ends with these 10 connecting wire ends. The connector assembly 363 electrically is connected by connecting to the connector 302. The connection between the assembly 363 and the connector 302 is carried out using a well-known method such as a zipper.

Figure 5B:
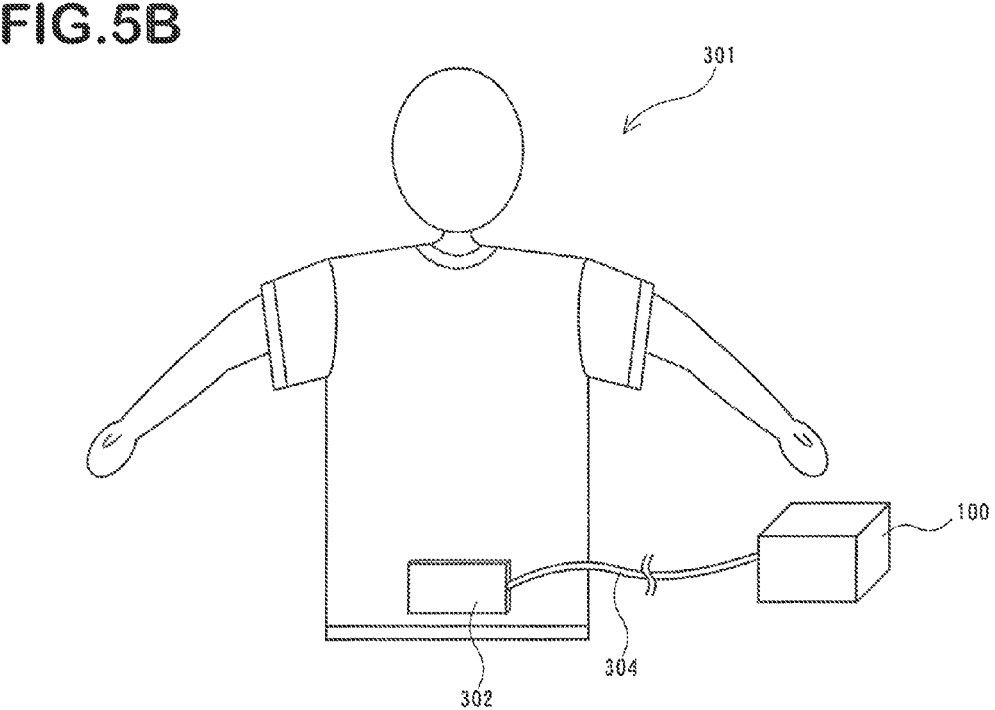
FIG. 5B is a view showing that the examinee wears the shirts.

FIG. 5B is a view showing the examinee wearing the biological information shirt 301. In order to carry out cardiogram measurement using the shirt 301, the assembly 363 of the shirt 301 is connected (attached) to the connector 302. Then the connector 302 is connected to the analysis device 100 via a power cable 304.

3-3. Cardiogram Measurement

Cardiogram measurement is carried out using the shirt 301 according to the first embodiment as described in the above. Such exemplary measurement is carried out as following procedures.

Electric potentials of the examinee acquired from the chest electrodes (353, 354, 355, 356, 357, and 358) and the four limb electrodes (351, 352, and 361, 362) are conveyed to an amplifier 11 through the analysis device 100. Noises are removed by a filter 19 from the amplified electric potential with the amplifier 11. The A/D converter 12 converts electric potential data (analog data) into digital data. The CPU 10 of the analysis device 100 records digital data acquired through the 10 electrodes into the memory 16 (or the F-ROM the following -- the same) sequential manner as cardiogram wave data, and then calculates a 12 lead cardiogram. The 12 lead cardiogram is a cardiogram in which 12 patterns of cardiograms are obtained by putting on a living body surface from several electrodes to more than a dozen of electrodes.

Figure 6:
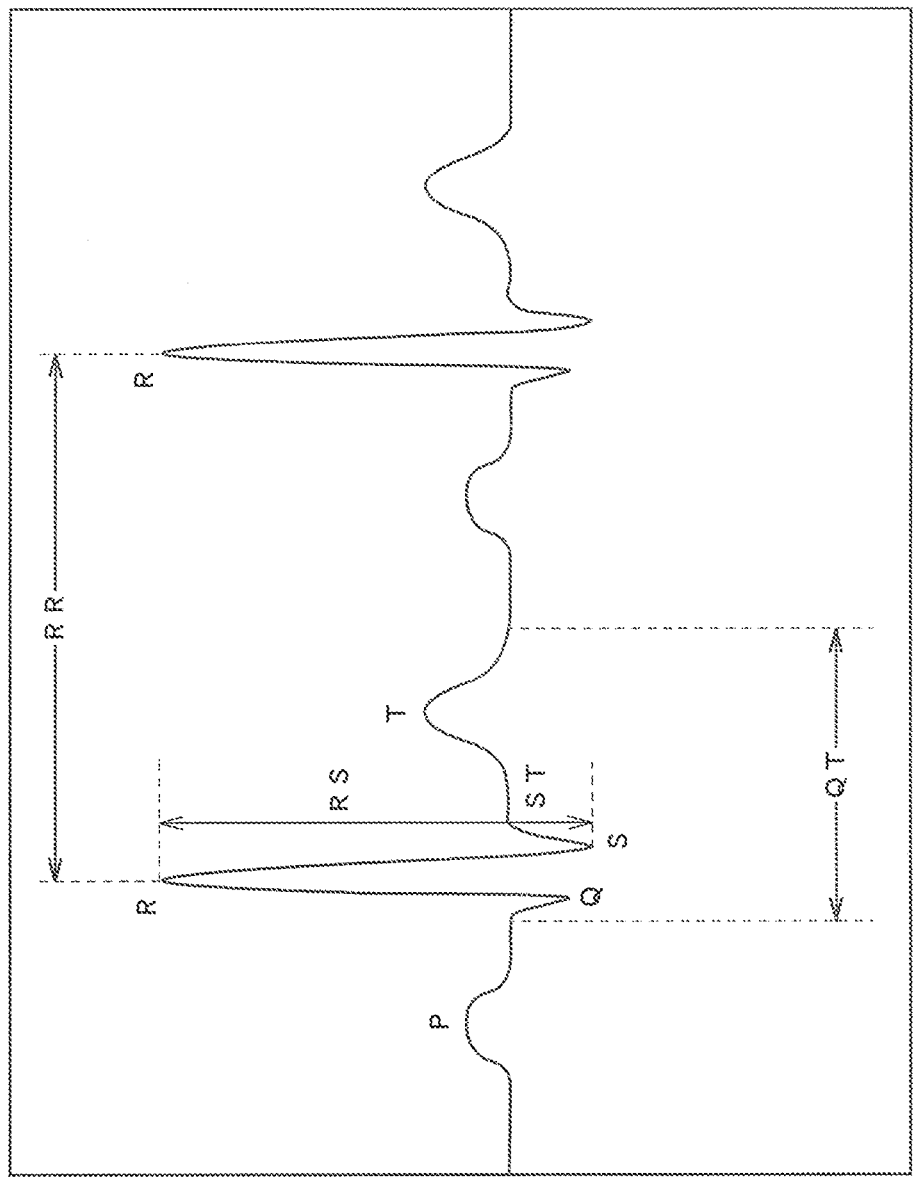
FIG. 6 is a graph showing a pattern diagram of a cardiogram waveform being stored.

FIG. 6 is a graph (longitudinal axis: electric potential (voltage), horizontal axis: time) showing cardiogram waveform data stored in the memory 16. The CPU 10 processes the cardiogram wave data shown in FIG. 6 so as to render the graph on a display 14. Rendering the cardiogram is carried out by moving the plotting point (to the right hand side of the display screen) as time progresses during a cardiogram measurement. Also, the CPU 10 recognizes the waveform for every one cardiac beat in accordance with the cardiogram wave data. As shown in FIG. 6, the CPU 10 recognizes (extracts) all of P (P-electric potential or P-wave height), (Q-electric potential or Q-wave height), R(R-electric potential or R-wave height), S(S-electric potential or S-wave height), T(T-electric potential or T-wave height), ST(ST-level), QT(QT-period), RR(RR-period), RS-amplitude value or a part of them as recognized value data (characteristics) and stores them into the memory 16. The CPU 10 recognizes one heart beat and each of the waves in the cardiogram by performing the following process when the waveform is found to be normal.

(1) Recognition of one heart beat: After sampling of cardiogram waveform data (electric potential values or voltage values) for a predetermined period, RR period is recognized as one heart beat through recognition of an R-wave representing the maximum component over a threshold value and upcoming R-wave (representing the maximum component over the threshold value). At that time, T-wave component (less frequency than the R-waves) that is one of the peak values may be removed with a filter by which lower frequency components are cut.

(2) P-wave: A wave exists at a position prior to 200~300 msec (milliseconds) from the R-wave is recognized as P-wave.

(3) Q-wave: The bottom value right before the R-wave is recognized as a Q-wave.

(4) S-wave: The bottom value right after the R-wave is recognized as an S-wave.

(5) T-wave: The peak value existing between the first R-wave and the second R-wave is recognized as a T-wave.

(6) ST-region: The maximum region between the S-wave and the T-wave are recognized as an ST-region when the S-wave and the T-wave are in linear interpolation.

In an cardiogram measurement, there might be high possibilities arising of high frequency noises having an abnormal cycle unexpectedly depending on behaviors of the examinee during the measurement and extraction of recognition value data not being correctly performed. In order to measure correct recognition value data without such high frequency noise, a technique disclosed in Japanese Patent Laid-Open Publication No. Hei06-261871 may be used.

Figure 7:
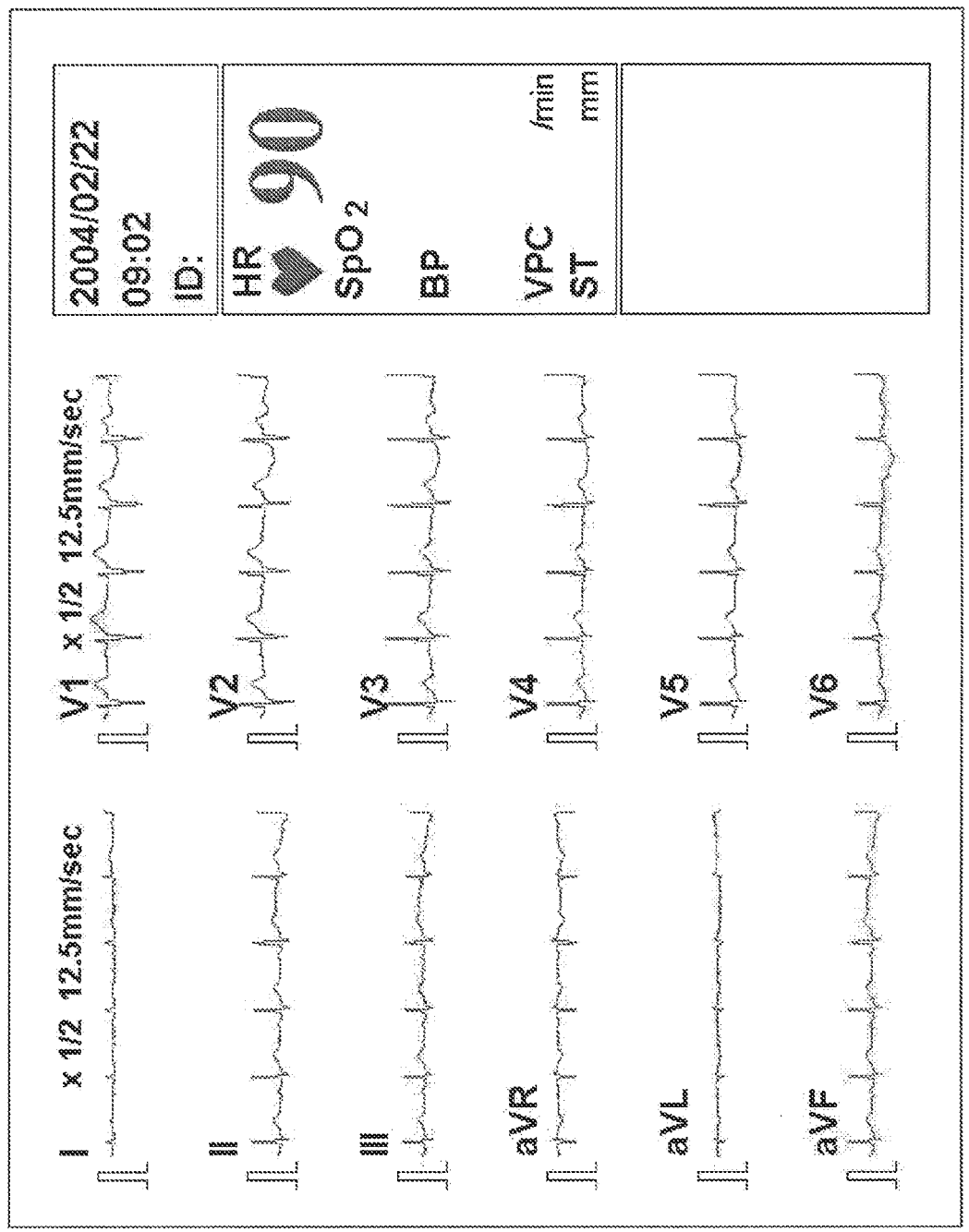
FIG. 7 is a view illustrating measurement results of cardiogram according to the first embodiment.

FIG. 7 is a view illustrating measurement results of cardiogram obtained with a shirt constructed similar to the biological information measurement shirt 301 shown in FIG. 4. In the drawing, cardiograms for the measurement of all the 12 kinds of leads standard limb leads (the I-lead, the II-lead, the II-lead), aV-leads (aVR, aVL, aF), chest-leads (V1, V2, V3, V4, V5, V6) are shown.

3-4. Advantages of the Embodiment

In the above described embodiments, longitudinally formed strip shaped chest electrodes are arranged around the front of the chest of an examinee (see FIG. 4). It is, therefore, possible to increase the possibilities of acquiring electric potentials of the heart through the longitudinally formed strip shaped chest electrodes having wide areas even if the constitution of each examinee varies and position of the heart moves and other unexpected change in conditions arises during the cardiogram measurement.

In the above described embodiments, the biological information measurement shirt 300 is employed as a biological information measuring garment. Also, because the shirt 300 is made of an elastic fabric, alignment and positioning of the electrodes and other parts may be performed easily due to its adhesion to the examinee's upper body. In addition, the possibility of changing the position of the electrodes to an examinee for each measurement is suppressed because a similar biological information measurement shirt is used for each measurement.

In the above described embodiments, the four limb electrodes have a larger area than the conventional electrodes and are arranged on positions corresponding to four limb leads. Cardiograms through the four limb leads can stably be acquired.

In the above described embodiments, both the four limb electrodes and the chest electrodes are formed so as to be thicker than the woven part 371. The thickness of these electrodes is not limited to that, such electrodes may be formed in a thickness so as to contact with the body surface of an examinee. But it is desirable to make the electrodes thicker than the woven part 371 and to increase elasticity for improving its adhesion to the body surface in order to suppress change in the position of the electrodes (decreasing noise). Further, from a viewpoint of increasing measurement sensitivity, it is preferable to make the electrodes thicker in order to increase the conductivity (lower its electric resistance).

3-5. Variation of the First Embodiment (1) Variation in Form of the Biological Information Measurement Shirt 301

FIG. 8 are a variation of the biological information measurement shirt 301 according to the first embodiment.

Figure 8A:
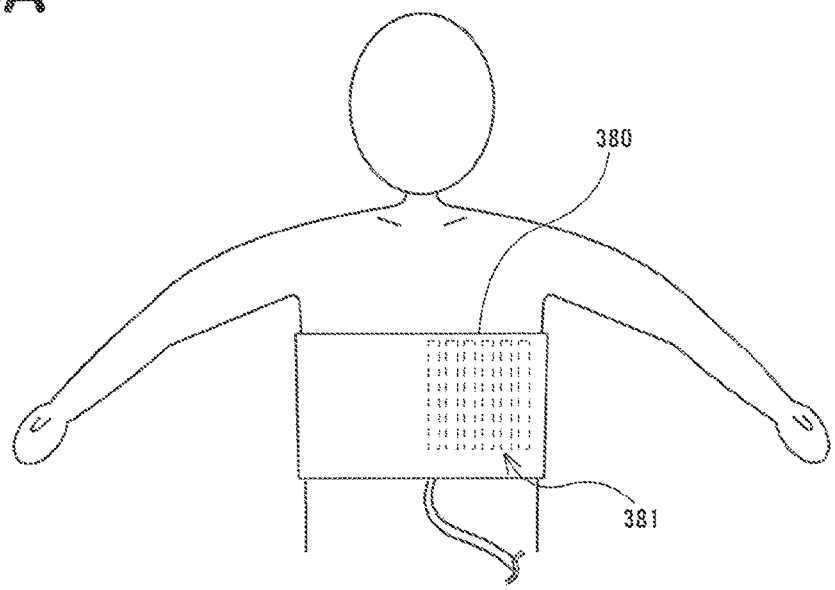
FIG. 8A is a variation of the shirt for measuring biological information according to the first embodiment.

FIG. 8A shows a garment 380 (during wear) formed as a biological information measuring garment according to the first embodiment. Similar to the shirt 301, a chest electrode 381 is knitted on the body surface side of the examinee in the garment 380. In this case, four limb electrodes (not limited to the four limb electrodes shown in FIG. 4A (351, 352, 361, 362)) separately need to be placed on the examinee.

Figure 8B:
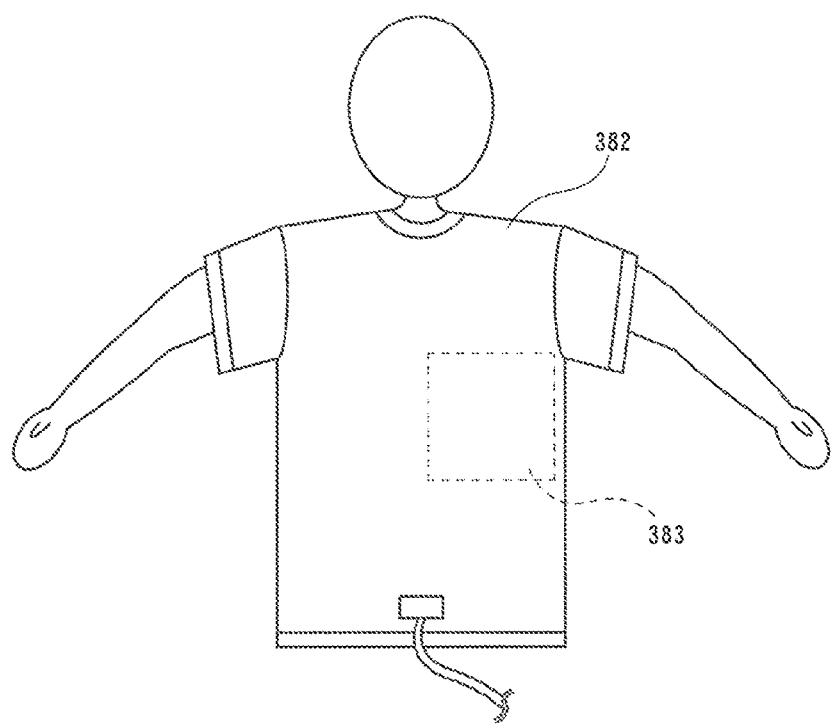
FIG. 8B is another variation of the shirt for measuring biological information according to the first embodiment.

FIG. 8B shows another biological information measurement shirt 382 (during wear) similar to the shirt 301 but the shirt 382 has a single chest electrode. The single chest electrode 383 is knitted on the body surface side of the examinee to nonconductive fabric of the shirt 382 similar to the shirt 301. The chest electrode 383 is arranged at positions so as to cover the body surface around the ribs on the anterior surface of the heart. Particularly, the electrode 383 covers from the body surface around a presternal region to the region around a thorax of the examinee for a perpendicular direction of the body axis and the electrode is assigned so as to covers the body surface around the fourth rib to that around the sixth rib (or around the seventh rib, or around eighth rib, or the lower border of the ribs).

Although, FIG. 8B shows a shirt having a single electrode as the chest electrode, other number for the chest electrode may be used. For another embodiment, chest electrodes consist of two or three electrodes, four or five electrodes may also be employed.

In the above described embodiments, the biological information measurement shirt 301 which is for a male adult, the size of which may be varied as appropriate when examinees are female and child. Beside, the biological information measuring garment may also be formed in a shape appropriate for underwear other than shirts, underwear for female (such as brassiere), or pajama (nightwear), or polo shirts and the like.

(2) Variation of Chest Electrodes and (or) Conductive Fabric of Four Limb Electrodes A fabric adhering silver particles (conductive fabric) which functions as the chest electrodes and the four limb electrodes is used in the first embodiment, alternatively, another conductive material may be used. For example, the chest electrodes and (or) the four limb electrodes may be formed of a fabric adhering a conductive material other than silver particles, metal plate to the shirt part 350, or attachment of a conductive film substrate (or a conductive printed board), or utilizing a conductive ink, or using fullerene evaporation coating. In addition, for connecting wires, a conductive material other than the above mentioned conductive fabric may be used.

Alternatively, a shield which can connect to the grounding wire (0 electric potential) may be attached (or knitted) to the front side of the shirt 301 in order to suppress the effects of noise other than bioelectric currents. Specifically, a part of the connector 302 is defined as a grounding terminal and the attached shield is connected to the defined grounding terminal. As an example of such shield, a fabric made of 100% on its surface and of electromagnetic shielding fabric (a trilaminar structured special fabric made of polyester monofilament, nickel, acryl ate membrane so on) is available.

(3) Variation of Weaving of Biological Information Measurement Shirt 301

In the above described embodiments, the shirt 301 is formed of, the biological information measurement shirt 301 is formed as a double cloth, but the method of weaving such shirt is not limited to that way. In an alternative embodiment any other desired weaving method such as a single cloth or triple cloth may be employed.

(4) Variation of Connector Structure

In the above described embodiments, an exemplary structure electrically connecting the electrodes and the analysis device 100 by bonding together the connector assembly 363 and the connector 302 is shown, such structure is not limited to that one. The method of connecting the connector assembly 363 and the connector 302 can be a predetermined structure by which both the components can mate each other. Specifically, such structure comprises wiring terminals of the connector assembly 363 made as metal plugs and the other connector 302 comprises jacks into which the metal plugs are inserted.

4. Second Embodiment

Cardiogram Measurement Processing

4-1. Biological Information Measurement Shirt

A biological information measurement shirt according to the second embodiment will be described herein. The second embodiment resolves problems related to an unexpected arrangement of the chest electrodes caused by a variation in the structure of each examinee or unfavorable body movement of an examinee and so on. The shirt 301 according to the second embodiment has a similar structure to the shirt 301 according to the first embodiment. Consequently, description of the second embodiment will be made focusing on a different portion from the first embodiment.

Figure 9:
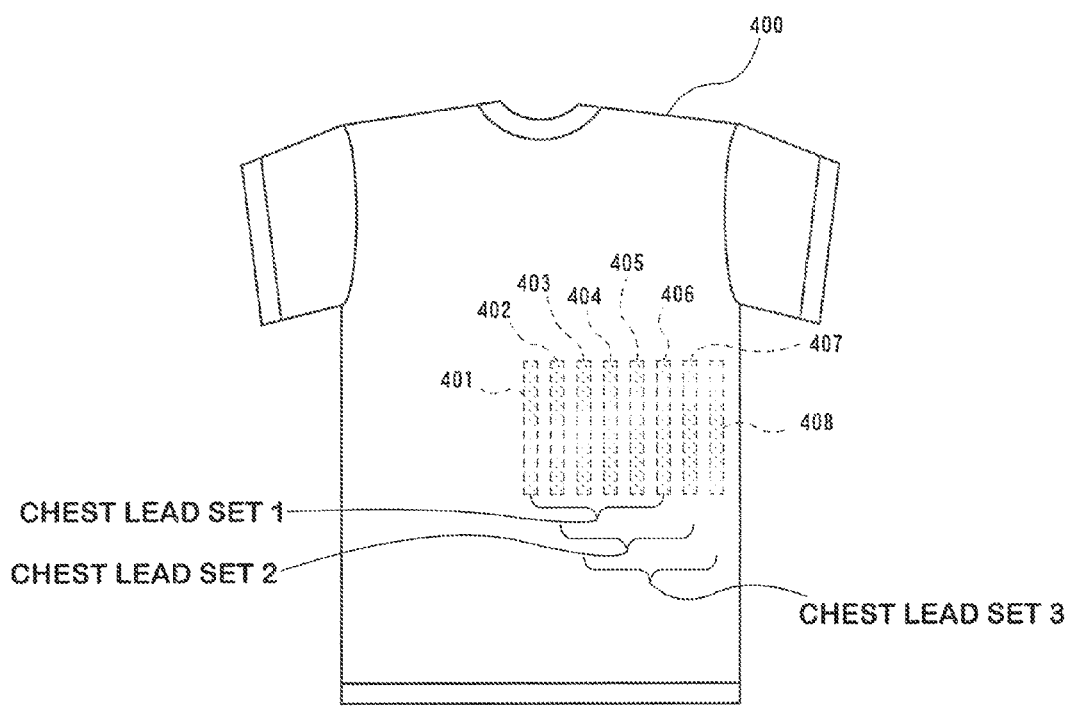
FIG. 9 is an overall view of a shirt for measuring biological information according to the second embodiment.

FIG. 9 is an overall view of the biological information measurement shirt 400 according to the second embodiment. The chest electrodes of the shirt 400 include a total of eight chest electrodes 401, 402, 403, 404, 405, 406, 407 and 408. Here, no description of a connector will be made. As for four limb electrodes for the second embodiment, not only the four limb electrodes used in the first embodiment, but also generally used silver/silver chloride electrodes may be employed.

As shown in FIG. 9, a combination of six of the chest electrodes 401, 402, 403, 404, 405, 406, another combination of six of the chest electrodes 402, 403, 404, 405, 406, 407 and still another combination six of the chest electrodes 403, 404, 405, 406, 407 and 408 are respectively defined as a chest lead set 1, a chest lead set 2 and a chest lead set 3. The arrangement of these chest lead sets 1, 2 and 3 can be represented as below, for example. Depending on the possibilities of variation in the structure of each examinee or unfavorable body movement, the area covered with the chest electrodes and the number there of may be varied.

Chest lead set 1: a region of covering the body surface from a position moved approximately for one chest electrode toward the right hand side of the presternal region of the examinee to a position vicinity of a chest lateral part.

Chest lead set 2: a region of covering the body surface from a position of the presternal region of the examinee to a position vicinity of a left chest lateral part (similar to the arrangement of the chest electrodes).

Chest lead set 3: a region of covering the body surface from a position moved approximately for one chest electrode from the left chest lateral part toward the left hand side of the presternal region of the examinee to a position vicinity of a chest lateral part.

4-2. Cardiogram Measurement Process

A flowchart describing a program of process for cardiogram measurement performed by the analysis device 100 according to the second embodiment will be described with reference to FIG. 10.

The CPU 10 starts the cardiogram measurement process and a timer (step S201). Then the CPU 10 measures cardiograms of chest leads through the chest electrodes 401 to 408 and the amplifier 11 and so on, and records to the memory 16 electric potentials for each of the chest electrodes (S203). Subsequently, the CPU 10 judges whether or not a waveform of one heart beat for each of the chest leads has been recognized (S205). The judgment in step S205 is similar to the process described in the first embodiment. If one waveform can not be recognized in step S205, the CPU 10 repeats the process from step S203.

When one waveform can be recognized in step S205, on the other hand, the CPU 10 judges whether or not the timer counts equal or more than 30 seconds (step S207). If the counted value is less than 30 seconds, the CPU 10 displays on the display 14 cardiogram waveforms (cardiogram graphs) in accordance with cardiogram data for outputting electric potentials of the selected chest lead set as cardiogram waveforms (S213). In the embodiment, it is assumed that the chest lead set 1 shown in FIG. 9 is selected as a default of the chest lead set.

Figure 13A:
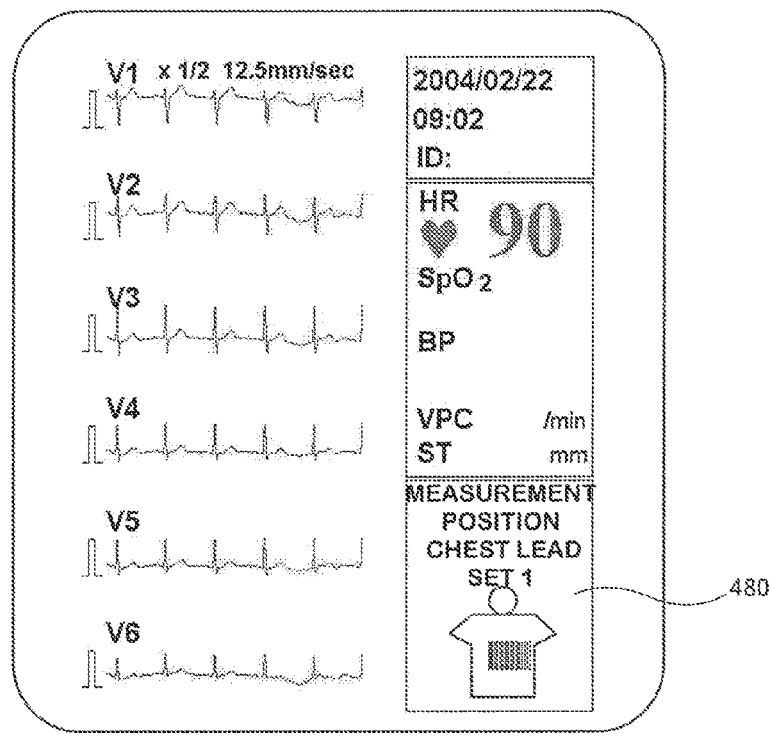
FIGS. 13A and 13B are display examples of data under processing of cardiogram measurement according to the second embodiment.

FIG. 13 are examples of displays on the display 14 under the cardiogram measurement process according to the second embodiment. FIG. 13A is an example of display of a cardiogram waveform of the chest lead in the process carried out at step S213. A measurement position guide 480 indicates the name of chest lead set currently be measured, a position of the chest electrodes corresponding to the currently used lead set (at a diagram illustrating the body of examinee). Specifically, in order to clearly illustrate the display of cardiogram waveforms in accordance with the chest electrodes 401, 402, 403, 404, 405 and 406 shown in FIG. 9 (waveforms according to the chest lead set 1), the measurement position guide 480 highlights (intensified display) positions of the corresponding electrodes within a diagram of upper body of the examinee. In the embodiments, upper body of the examinee is used for such display, but any other display can be used. For another embodiment, a diagram illustrating the biometric information measurement shirt can be used. Further, display method of such diagram (display image) can be changed to any well-known method to the person skilled in the art.

Subsequently, the CPU 10 judges whether or not that there is cardiogram data (unprocessed data) which is not displayed on the display 14 (S215). If there is unprocessed data, the CPU 10 repeats the process from step S203.

If the counted value is judged more than 30 seconds at step S207, the CPU 10 carries out a process for selecting the chest lead set at step S209.

FIG. 11 is a flowchart of a program for selecting the chest lead set which is indicated as a sub-routine at step S209 of FIG. 10. The CPU 10 calculates an amplitude value of each heart beat within a measurement range (30 seconds, herein) by acquiring an R-potential and an S-potential of a heart beat recognized at step S205 in FIG. 10 for each heart beat (S250). The amplitude value is calculated based on an equation: |R-potential−S potential|(the absolute value of the difference of R-potential and S potential). Such amplitude value corresponds to R-S distance shown in FIG. 6.

FIG. 12A is a diagram showing an exemplary record 450 of an RS amplitude value calculated by the CPU in step S250. Here, the term "Data No." is the number for specifying each heart beat recognized by the CPU 10 as time progress. Chest leads No. 1, No. 2, No. 3, No. 4, No. 5, No. 6, No. 7 and No. 8 show the chest leads respectively obtained according to the chest electrodes 401 shown in FIG. 9, the chest electrodes 402, the chest electrodes 403, the chest electrode 404, the chest electrode 405, the chest electrode 406, the chest electrodes 407 and the chest electrode 408. Here, RS amplitude values (measure: mV) for each lead are recorded to the memory 16 for heart beat numbers 1501 through 1530.

Subsequently, the CPU 10 calculates a total of the amplitude values for each of the chest leads (S252). Specifically, the CPU 10 adds all the RS amplitude values of the heart beat numbers 1501 through 1530 for each leads. FIG. 12B shows data record 452, a total of the RS amplitude values calculated by the CPU at step S252.

The CPU 10 calculates a total of the amplitude values of the chest lead set 1 (leads No. 1 through 6) (S254). The CPU 10 also calculates a total of the amplitude values of the chest lead set 2 (leads No. 2 through 7) (S256). Subsequently, the CPU 10 further calculates a total of the amplitude values of the chest lead set 3 (leads No. 3 through 8) (S258). FIG. 12C shows data record 454 of the RS amplitude values calculated by the CPU at step S254, S256 and S258.

Then, the CPU 10 specifies a chest lead set having the peak value for the total of the amplitude values (S260). When it is specified that the chest lead set 1 has the peak value, the CPU 10 selects the chest lead set 1 (S262). When the chest lead set 2 has the peak value is specified, the CPU 10 selects the chest lead set 2 (S264). When it is specified that the chest lead set 3 has the peak value, the CPU 10 selects the chest lead set 3 (S266). Here, it is judged that a total value (111.05) of the RS amplitude for the chest lead set 2 is the peak value as shown in FIG. 12C. The CPU 10 carries out a process from step S211 shown in FIG. 10 after carrying out step S264.

Figure 13B:
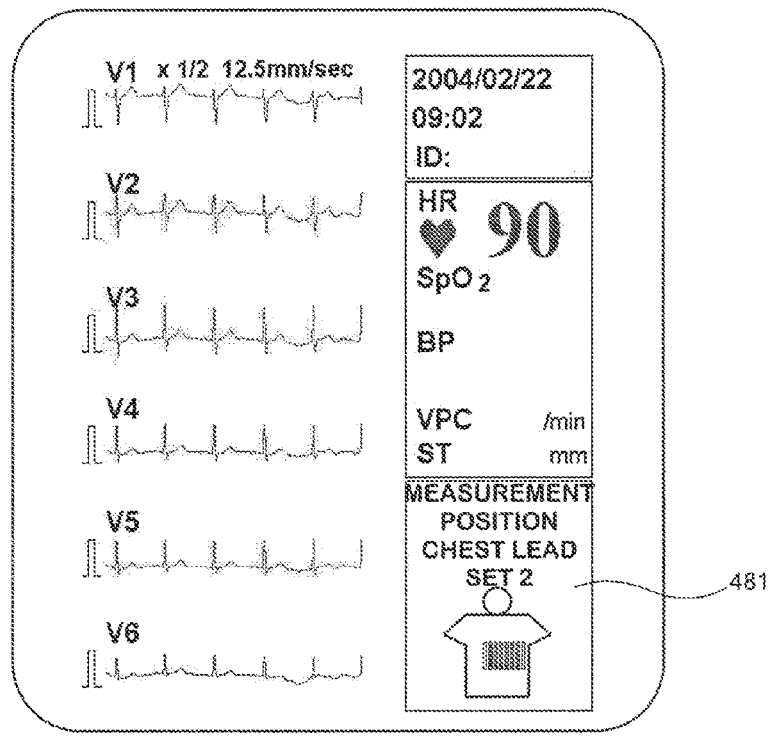

After execution of step 209, and resetting and restarting the timer (S211), the process at step S213 is carried out. Here, the cardiogram waveform is displayed on the display 14 in accordance with the cardiogram data of the chest lead set 2 selected at the step S264 of FIG. 11. As shown in FIG. 13B, in order to indicate that cardiogram waveforms (cardiogram waveforms according to the chest lead set 2) in accordance with the chest electrodes 402, 403, 404, 405, 406 and 407 are currently displayed, the guide 481 highlights (intensified display) positions of the corresponding electrodes within the diagram of upper body of the examinee. The CPU 10 ends the process when no unprocessed data exist at step S215.

4-3 Advantages of the Embodiment

By carrying out the process of selecting the chest lead set, the CPU 10 sets the selected information as the base of cardiogram outputs, after choosing information having a large RS amplitude value acquired from a plurality of the chest electrodes. Consequently, an appropriate chest lead can be selected regardless of variations of the constitution of each examinee (variation of the heart position) and that of the heart position due to movement of the examinees.

4-4. Variation of the Second Embodiment

Figure 14:
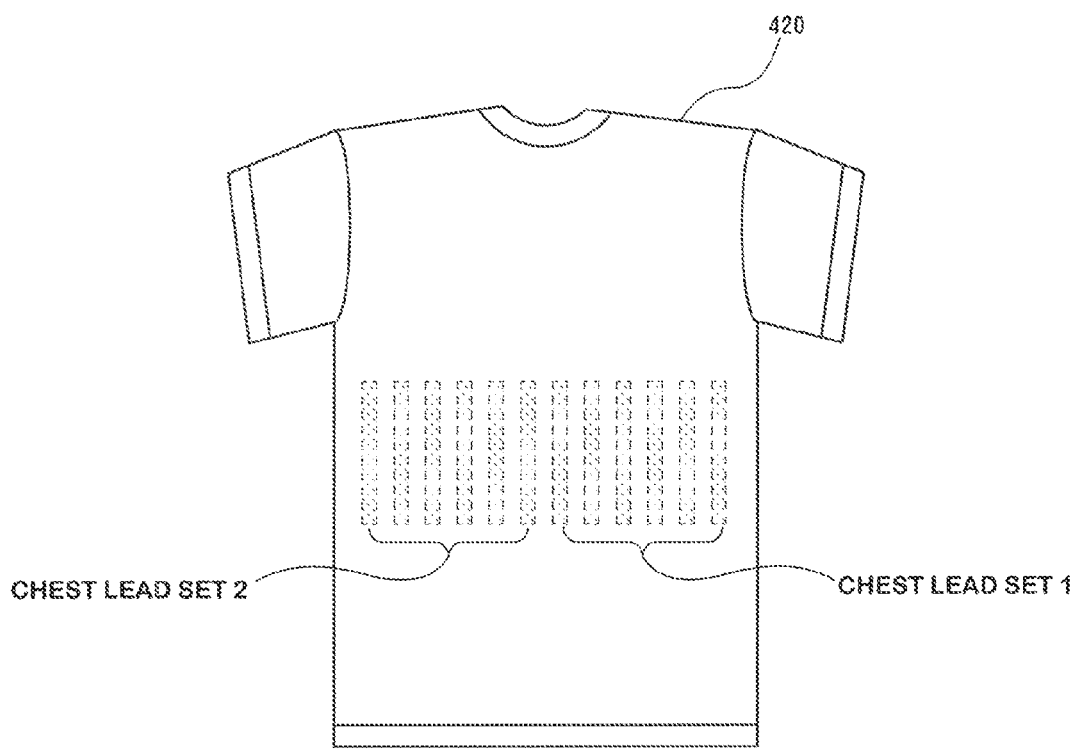
FIG. 14 is a variation of the shirt for measuring biological information according to the second embodiment.

FIG. 14 is a variation of the shirt 400 according to the second embodiment. A biological information measurement shirt 420 is formed so that the chest electrodes are arranged all over the chest of an examinee. Specifically, a total of twelve of the chest electrodes are arranged at position so as to cover the body surface from around left thorax of the examinee to right thorax thereof. The six chest electrodes to the right of the drawing are set to the chest lead set 1 and the remaining six chest electrodes to the left of the drawing are set to the chest lead set 2. Similar processing is carried out for the cardiogram measurement processing in the flowchart shown in FIGS. 10, 11.

According to this variation, the analysis device 100 can display waveforms of the cardiogram acquired with the selected chest lead set after selection of a chest lead set acquiring a large a large amplitude value (an RS amplitude value, for example). With this variation, not only an examinee that has the heart in left-hand side but an examinee that has the heart in right-hand side can measure the cardiogram.

(2) Variation of Chest Lead Set Selection

In the second embodiment, a chest lead set acquiring a large RS amplitude values in total is selected out of combinations of the chest lead sets 1 to 3 shown in FIG. 9, but the embodiment is not limited that way. A variation of the chest lead set selection described as follow can be employed.

Selection of each chest lead: Selection for each lead based on the chest electrodes, not for each of the chest lead sets, is carried out. In the case of the shirt 400 shown in FIG. 9, cardiogram data through at most eight leads are acquired and the data having six largest RD amplitude values are selected.

Selection of chest lead according to a reference RS amplitude value: only the cardiogram data having more RS amplitude value than a predetermined reference value (0.5 mV for example) is selected out of each chest lead set (or each lead based on the chest electrodes).

Measurement range (30 seconds in this embodiment) to be a subject of an RS calculation period by the CPU 10 in step S250 of FIG. 12 can be set any period.

For example, the process for cardiogram measurement show in FIG. 11 can be carried out per one heart beat. Also, the calculating method for RS amplitudes can be changed to any other method such as calculating average values and the like other than the method described in the second embodiment such as calculating total values. Further, the difference between R-potential and S-potential is an example of an amplitude value of the heart beat in the embodiment, other values (such as a difference between an R value and a Q value, the absolute of an R value and so on) can be employed.

5. The Third Embodiment

Respiration Rate Measurement Processing

5-1. Biological Information Measurement Shirt

Figure 16A:
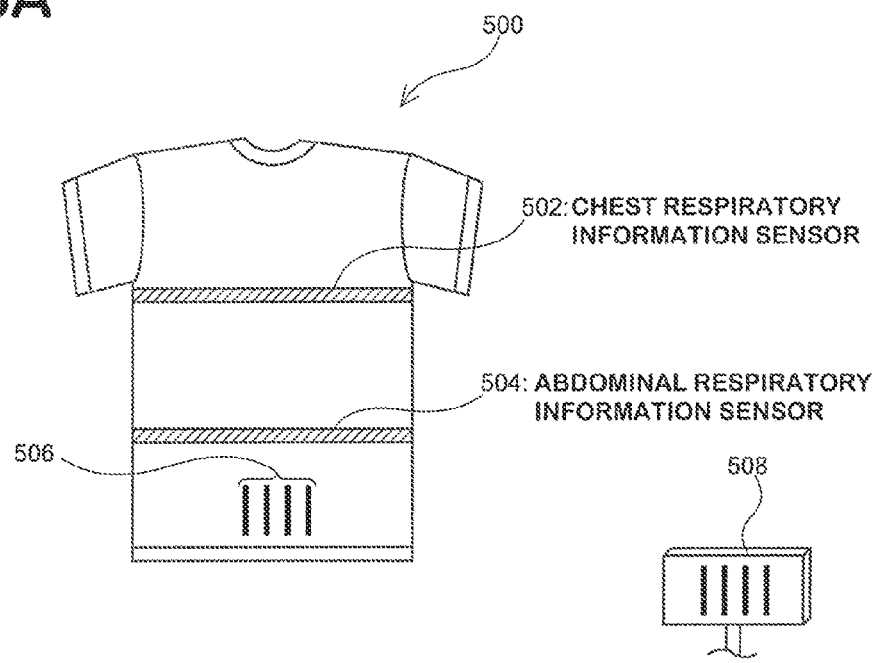
FIG. 16A is an overall view of a shirt for measuring biological information according to the third embodiment and FIG. 16B is a view showing that the examinee wears the shirts.

A biological information measurement shirt 500 according to the third embodiment will be described herein. The overall dimension of the shirt 500 is shown in FIG. 16A. The shirt according to the third embodiment comprises a structure for measuring a respiration value. The connectors, the shirt part and the analysis device connected thereto are the same as the ones described in the first embodiment. As a consequence, the following description mainly focuses on parts different from the first embodiment.

FIG. 15A is a partial view of the shirt 500 for measuring biological information according to the third embodiment. Specifically, FIG. 15 A shows the front body (chest side) of the biological information measurement shirt 500 in the manufacturing process thereof before cutting. The shirt 500 consists of a shirt part 550 formed of an elastic fabric having a nonconductive property and an electrode part described later. In the shirt part 550, a chest respiratory information sensor 502 formed of a conductive fabric and an abdominal respiratory information sensor 504 formed of a conductive fabric are knitted therein. Here, a fabric adhering (through chemical binding, for example) metal particles (silver particles, copper particles, or copper sulfide particles, for examples) there on (for example Thunderron (registered Trademark) manufactured by Nihon Sanmo Dyeing Co., Ltd. is used in the embodiments.

The chest respiratory information sensor 502 and the abdominal respiratory information sensor 504 are connected through connecting wires of a conductive material to an connector assembly part as an assembly of terminals of wires. In this embodiment, a conductive fabric similar to that forming the sensors 502 and (or) 504 is employed for the wires and the connector assembly 506, for example. One terminal of the sensor 502 is connected through a wire 554 to a connector assembly 506, and the other terminal is connected via a wire 552 to the connector assembly 506. Similarly, the sensor 504 is connected via a wire to the connector assembly 506.

It is preferable for the chest respiratory information sensor 502 and the abdominal respiratory information sensor 504 in the shirt part 550 of the shirt shown in FIG. 15A to be arranged on places where expansion and contraction of the shirt become large by respiratory of the examinee at the time of wear. Specifically, the places, where change (circumferential merit change of chest) of the girth-of-the-chest length by the examinee's breathing and change of abdominal circumference length become large, are desirable. The shirt 500 mainly expands and contracts toward a direction perpendicular to the body axis of the examinee (chest circumference direction). Therefore, as for the shirt, it is desirable to form so that the rate of expansion and contraction toward a direction perpendicular to the body axis of the examinee (chest circumference direction) may become larger than that toward the body axis of the examinee (toward the length of the shirt).

FIG. 15B is a partial sectional view taken on a direction A-A of FIG. 15A. In this embodiment, the shirt is formed of as a double cloth shirt, for example. The shirt part 550 is formed as a single cloth fabricated by piling a woven part 560 of a nonconductive fabric and another woven part 561 thereof. The chest respiratory information sensor 502 is knitted between the woven parts 560 and 561. The connecting wires 552 and 554 respectively knitted to both ends of the sensor 502. Another chest respiratory information sensor 504 and a connecting wire therefrom are formed of as a double cloth.

FIG. 15C is a partial sectional view taken on a direction B-B of FIG. 15A. A part contacting with the connector assembly 506 of the woven part 560 is defined as a terminal part of the connecting wiring in that fabric. The connector assembly 506 is knitted so that it contacts with the woven part 560. The connecting wires wiring from each of the electrodes are knitted at positions so as to be sandwiched between the woven part 560 and the woven part 561 (see FIG. 15B), they are electrically connectable to the connector assembly 506 by knitting a part of the woven part 560 at a part connecting with the connector assembly 506.

Manufacturing process of the biological information measurement shirt is sequentially carried out under the following steps: (1) forming the shirt part 550 including a step of knitting the chest respiratory information sensors 502 and 504; (2) forming the front part by cutting a resultant of the step (1); (3) forming the back side, sleeves and collar and other details; (4) sewing each of the front side, the back side, the sleeves and the collar of the back side. Conventional technologies to a person skilled in the art such as knitting by hand (or) using a computer controlled sewing machine may be employed for the step "(1) forming the shirt part 550 including a step of knitting the chest respiratory information sensors 502 and 504" in the manufacturing process.

5-2. Biological Information Measurement Shirt 500 (Overall View)

FIG. 16A is an overall view of the shirt 500 that includes the above described shirt part 550. The shirt 500 comprises the chest respiratory information sensor 502 and the chest respiratory information sensor 504 and the connector assembly 506. The connector assembly 506 has a total of four wire terminals so as to electrically connect with both terminals of the sensors. A connector 508 has a total of four electro terminals for respectively connected to these four wire terminals. The connector assembly 506 is electrically connected by contacting to the connector 508. The contact between the connector assembly 506 and the connector 508 is done by a well-known mean utilizing using a well-known method such as a zipper.

Figure 16B:
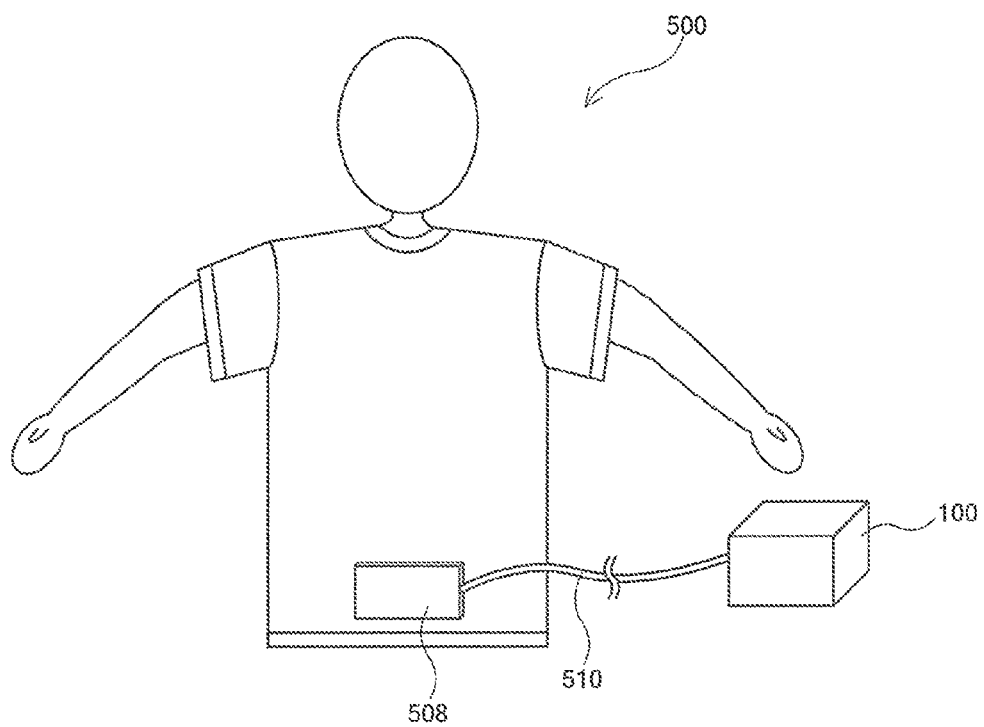

FIG. 16B is a view showing that the examinee wears the shirt 500. In order to carry out respiration measurement using the shirt 500, the assembly 506 of the shirt 500 is connected to the connector 508. Then the connector 508 is connected to the analysis device 100 via a power cable 510.

5-3. Respiration Measurement

Respiration measurement is carried out using the above described shirt 500. Such exemplary measurement is carried out as following procedures.

Upon an examinee wearing the shirt 500 (see FIG. 16), the connector 508 is connected to the connector assembly 506. The connector 508 is formed of a similar structure to that of the connector 302 shown in FIG. 3. Such connector 508 is connected to the analysis device 100 via the power cable 510 (see FIG. 3).

A certain electric current (a very small current such as 10 μA range) is applied from the power supply 20 to the chest respiratory information sensor 502 and (or) the chest respiratory information sensor 504 through the power cable 510, the connector 508, the connector assembly 506 (application of a very small current).

The form around a girth-of-the-chest length or that of an abdominal circumference length may vary in response to respiration of the examinee. Such variation of the forms generally includes a change of the girth-of-the-chest length and (or) the abdominal circumference length, for example. In response to the change, the chest respiratory information sensor 502 and the chest respiratory information sensor 504 are deformed. Deformation of each sensor generally includes change in length of horizontal direction (the girth-of-the-chest length or the abdominal circumference length) of the sensors.

As an example, both the chest respiratory information sensor 502 and the chest respiratory information sensor 504 are formed of a conductive fabric adhering metal particles thereon. As a consequence, since the chest respiratory information sensor 502 and the chest respiratory information sensor 504 made a turning-on-electricity state by the power supply 20 responds to deformation of the sensors accompanying respiration of the examinee and the number of contact of metal particles increases or decreases, the resistance value of each sensor has changed. For example, as the girth-of-the-chest length (or the abdominal circumference length) becomes long, the amount of contact of the metal decreases, the electric resistance thereof increases (current becomes hard to flow), after girth-of-the-chest length (or the abdominal circumference length) has become short conversely, the amount of contact of metal increases again, and the electric resistance thereof decreases (current becomes easy to flow). In the case of not using a conductive metal fabric, electric resistance of each conductive fabric changes with expansion and contraction of the length (or cross-section area) of the conductive fabric in response to the examinee's breathing. As described in the above, the shirt part 550 of the shirt 500 is formed of an elastic fabric having a nonconductive property. In order to enlarge the amount of change of the sensor form in response to the examinee's breathing, as for the shirt part 550, it is desirable to have sufficient elasticity so as to fit on the examinee's upper body. Beside, detecting sensitivity of respiration may be increased by enlarging the area of the chest respiratory information sensor 502 and the chest respiratory information sensor 504.

The resistance value sensor 21 (FIG. 3) senses variation of electric resistances of the chest respiratory information sensor 502 and the chest respiratory information sensor 504. The variation of electric resistance thus sensed is converted into digital data (electric resistance data) with the A/D converter 12.

Figure 17:
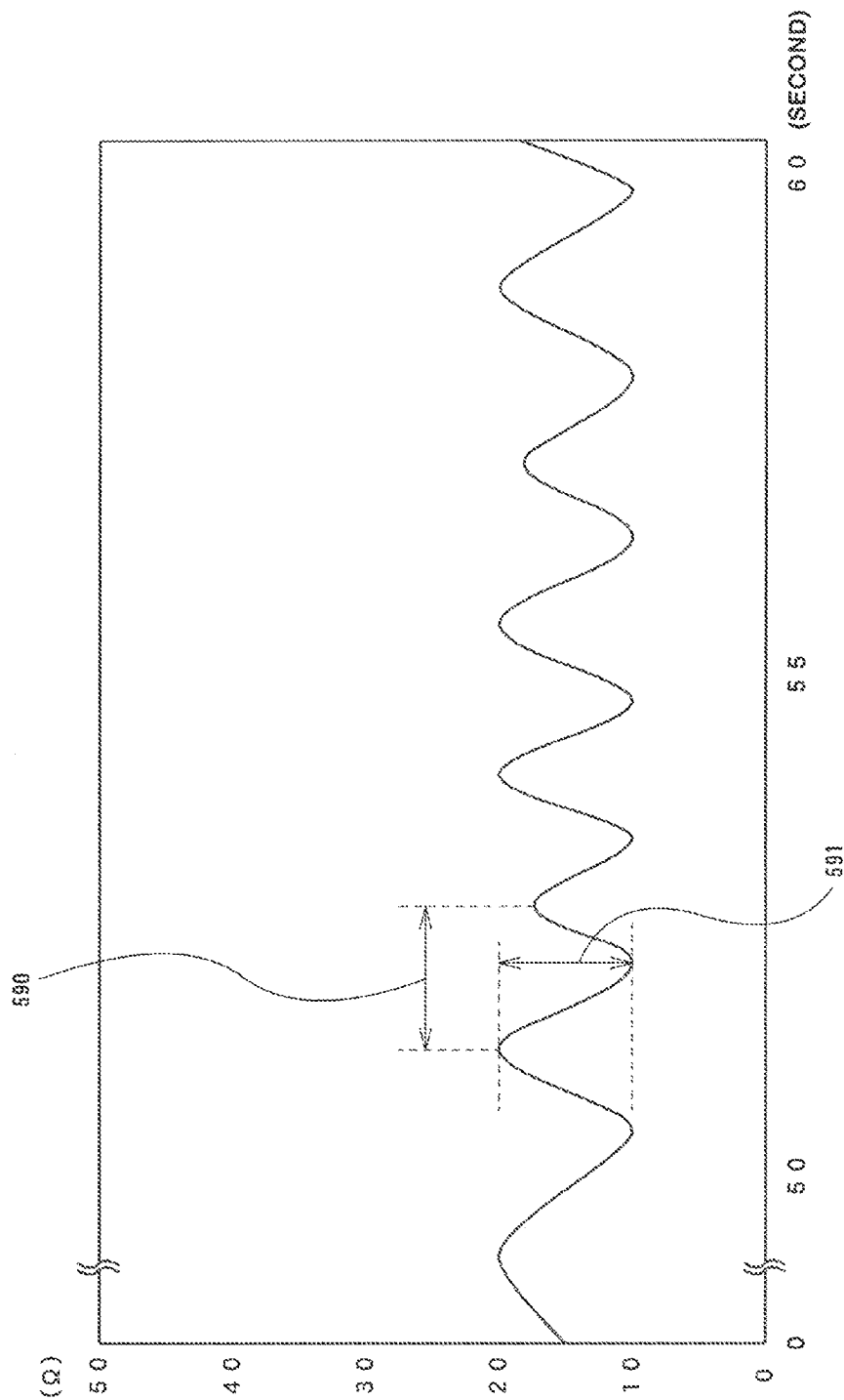
FIG. 17 is a graph schematically showing respiration rates being recorded.
Figure 18:
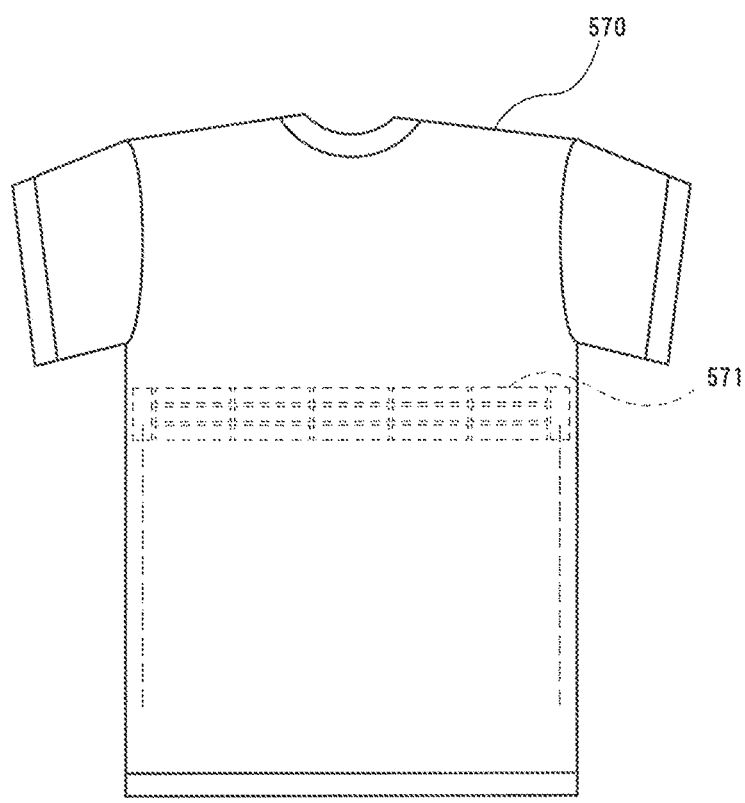
FIG. 18 is a variation of the shirt for measuring biological information according to the third embodiment.

FIG. 17 is a graph schematically showing respiration rates being recorded on the memory 16 of the analysis device 100. The drawing shows that variation of electric resistance of either one of the chest respiratory information sensor 502 and the chest respiratory information sensor 504 arises on a periodic basis. Such variation is defined as an electric resistance period part 590, an electric resistance amplitude part 591, and so on.

The CPU of the analysis device 100 calculates frequencies of the resistance variation in accordance with the resistance data and outputs respiration values based on the calculation results. Specifically, if the frequency of the resistance value is fifteen times per minute, the respiratory rate is defined as 15 (times/min.). Then, the analysis device 100 outputs information on the examinee such as the respiration rate to the display 14. Although, variation of electric resistance is sensed in the embodiment, it is not limited to that way. As another way, the analysis device 100 may compute the variable period of current (or voltage), and may output the number of respirations (or estimated respiration rate, the following -- the same) based on the result by detecting the current value (or voltage of each sensor) of each sensor.

An example of utilizing both means such as the chest respiratory information sensor 502 and the chest respiratory information sensor 504 in order to obtain respiration rate is described in this embodiment, the present invention is not however limited thereto. As another embodiment, it is possible to acquire the respiration rate based on the information from either one of the chest respiratory information sensor 502 and the chest respiratory information sensor 504. Generally, when a change of girth-of-the-chest length by the examinee's breathing is large, the chest respiratory information sensor 502 is adopted, and the chest respiratory information sensor 504 is used when the change of the abdominal circumference length is large. Besides, the analysis device 100 may output two pieces of respiratory information together in accordance with the two sensors, or, the device may output one of the respiratory information by a predetermined judgment means (by which a larger respiration rate is selected).

Advantage of the Embodiment

In the above described embodiment, respiration rate can be measured based on signals from the chest respiratory information sensor 502 (or the chest respiratory information sensor 504) arranged on the biological information measurement shirt (by detecting deformation of the sensor(s) as movement of a chest or an abdomen as breathing movement). It is, therefore, possible to measure respiration rate with less strain to the examinee even simple structure.

In the above described embodiment, as shown in FIG. 15B, the chest respiratory information sensor 502 (or the chest respiratory information sensor 504) is knitted between the woven part 560 made of nonconductive fabric with elasticity and the woven part 561. Consequently, the examinee does not contact each of the sensors, so that the electric influence to the examinee and the influence of the noise to electric resistance can be suppressed.

5-5. Variations of the Third Embodiment

FIGS. 18 through 23 are variations of the biological information measurement shirt 500 according to the third embodiment. The shirt 570 shown in FIG. 18 comprises a chest respiratory information sensor 571 made as fragments of conductive material on around an examinee's chest. Specifically, the sensor 571 is arranged at a position so that each of the conductive material fragments contacts with one another (breathing out state or the like) when the examinee's girth-of-the-chest length is its minimum, and the conductive material fragments apart from one another (breathing in state or the like) when the girth-of-the-chest length is in increase. Such conductive sensor 571 is made of a conductive film substrate and the like. Electric resistance of the sensor 502 varies as a result of repeating contact and no contact of the whole or part of the conductive fragments with the examinee's breathing. The analysis device 10 acquires respiration rates in accordance with the variation of the electric resistance. The sensor may be arranged not only to around the chest but also around the abdomen. In addition, the sensor 571 may be formed not only in a shape that the conductive material is arranged a parallel manner on the examinee's girth-of-the-chest direction, but also in a shape that the conductive material is arranged a zigzag manner (in a zigzag line).

Figure 19A:
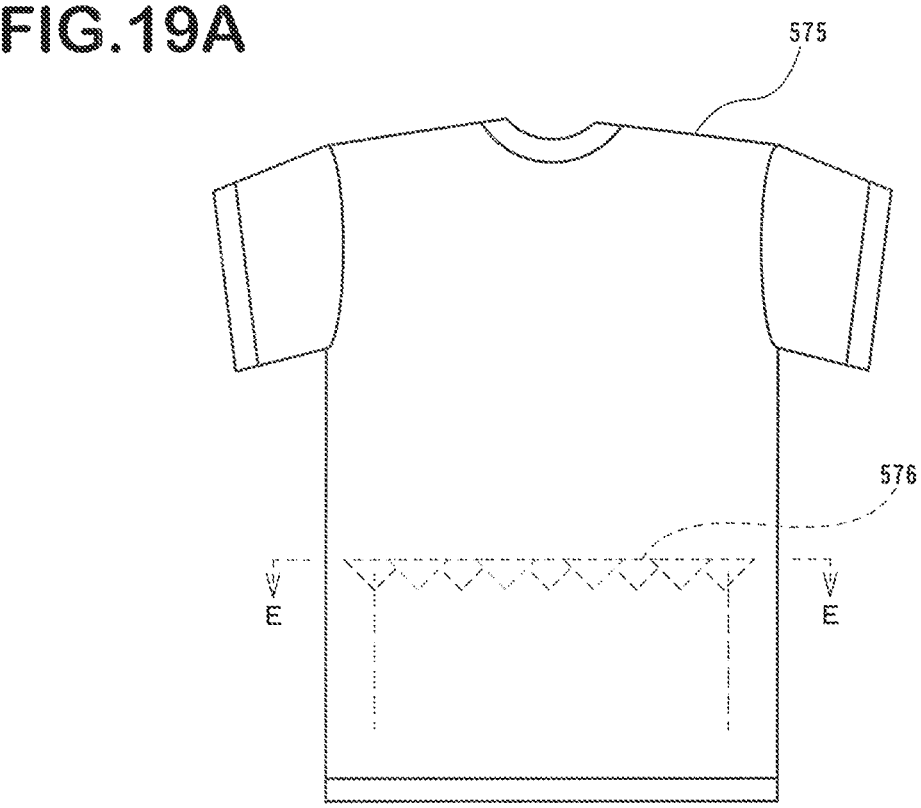
FIG. 19A is another variation of the shirt for measuring biological information according to the third embodiment.

A biological information measurement shirt 575 shown in FIG. 19A comprises an abdominal respiratory information sensor 576 made as fragments of conductive material on around an examinee's abdomen. Specifically, the sensor 576 is arranged at a position so that the contact area of the fragments is large when the examinee's abdominal length is short and the contact area of the fragments is in small because the fragments are apart from one another when the examinee's abdominal length is long. The biological information measurement shirt 575 is formed as a double cloth shirt, for example.

Figure 19B:
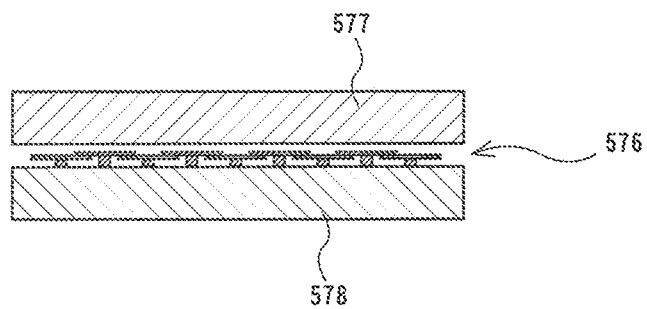
FIG. 19B is a sectional view taken on a direction E-E of FIG. 19A.

FIG. 19 B is a sectional view taken on a direction E-E of FIG. 19A. The short 575 is formed as a single cloth fabricated by piling a woven part 577 of a nonconductive fabric and another woven part 578. Such woven part 578 is on a side to which the body surface of an examinee is in contact. A part of the fragments of conductive material in the sensor 576 functions as an anchor (support) as a result of attaching them to the woven part 578, and a conductive wing (a plate part) is attached to the anchor. Such conductive wing contacts with another conductive wing adjacent thereto. The conductive sensor 576 (or its conductive wing) is formed of a conductive film, for example. Electric resistance of the sensor 576 varies as a result of repeating contact and no contact of the whole or part of the conductive fragments with the examinee's breathing. The analysis device 100 acquires respiration rates in accordance with the variation of the electric resistance. The sensor 576 may be arranged not only to around abdomen but also on around chest.

In the above described embodiment, the conductive wing (including the anchor part) is attached to the woven part 578, but the conductive wing (including the anchor part) may be formed by knitting a conductive fabric therein. In this case, since area of the wing which spreads only cannot be secured by knitting but the thickness of wing becomes unexpectedly thicker, so that it is preferable to carry out processing which makes flat the portion to be the wing with heat (so called calendar processing).

Figure 20:
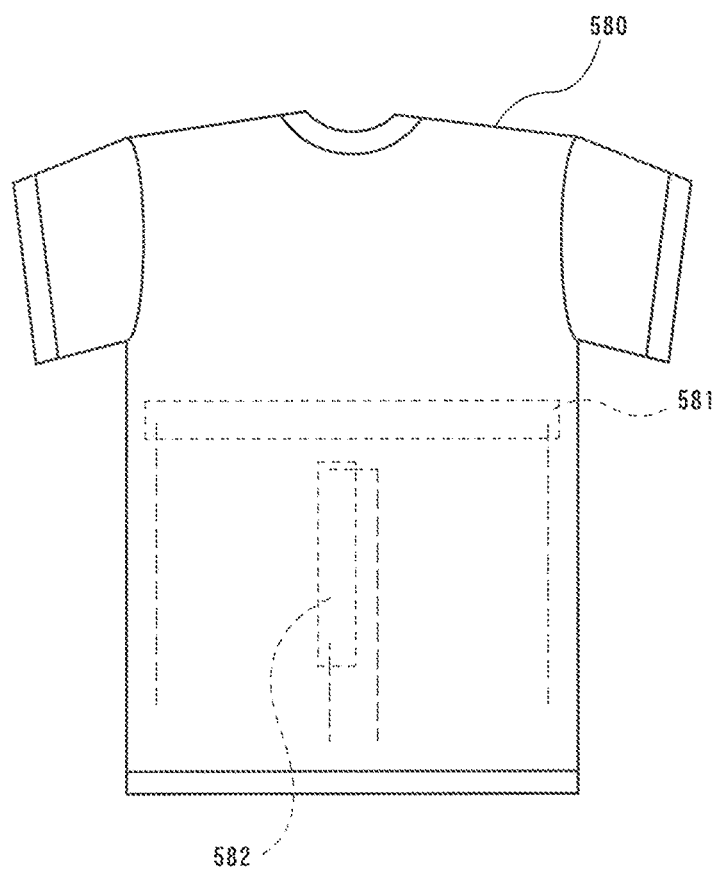
FIG. 20 another variation of the shirt for measuring biological information according to the third embodiment.

A biological information measurement shirt 580 shown in FIG. 20 comprises an abdominal respiratory information sensor 581 in a direction toward the girth-of-the-chest and another abdominal respiratory information sensor 582 in a direction toward the body axis (longitudinal direction) around the abdomen. Knitting the sensors into the shirt 580 and material of the sensors are the same to the ones described in the third embodiment. Electric resistance of the sensor 581 or the sensor 582 varies as a result of extraction and contraction thereof with the examinee's breathing. The analysis device 100 acquires respiration rates in accordance with the variation of the electric resistance. Such analysis device 100 may output two pieces of respiratory information together in accordance with the two sensors, or, the device may output one of the respiratory information.

6. Fourth Embodiment

Respiration Rate Measurement Processing (in Combination with Cardiogram R-Wave Analysis)

6-1. Biological Information Measurement Shirt

A biological information measurement shirt according to the fourth embodiment will be described herein. The fourth embodiment the reliability of the respiratory value measurement increases by combining the respiratory value measurement processing of the third embodiment with R wave analysis of cardiograms. The shirt according to the fourth embodiment comprises chest electrodes and four limb electrodes similar to that of the biological information measurement shirt 301 of the first embodiment (see FIG. 4A) and a chest respiratory information sensor similar to the sensor 502 of the biological information measurement shirt 500 of the third embodiment (see FIG. 15A). As a consequence, the following description mainly focuses on parts different from the first and the third embodiments.

FIG. 21 is an overall view of a biological information measurement shirt 600 according to the fourth embodiment. The shirt 600 comprises a chest lead set 603, a four limb lead set 604, a chest respiratory information sensor 601 and an abdominal respiratory information sensor 602. The chest lead set 603 and the four limb lead set 604 are the same as that used in the first and the second embodiments, each formed of six of chest lead electrodes and four of four limb lead electrodes. The sensors 601 and the 602 are the same as that used in the third embodiment. Here no description on connectors and related parts will be made. For the four limb lead electrodes, generally used silver/silver chloride electrodes may be employed instead of the four limb lead set 604.

6-2. Respiration Rate Measurement Processing

A flowchart describing a program for processing respiration rate measurement performed by the analysis device 100 according to the fourth embodiment will be described with reference to FIGS. 22 through 24.

The CPU 10 starts respiration rate measurement process and a timer (step S400). Then the CPU 10 acquires electric resistance values (respiration data) through chest respiratory information sensor 601 and an abdominal respiratory information sensor 602, and records them to the memory 16 (S402). Such process performed at S402 is the same as that described in the respiration rate measurement process described of the third embodiment.

Then the CPU 10 measures cardiograms of chest leads through the chest lead set 603 the four limb lead set 604 and the amplifier 11, and records to the memory 16 electric potentials for each of the chest electrodes (S404). Subsequently, the CPU 10 judges whether or not the waveform of one heart beat for each of the chest leads is recognized (S406). The judgment in step S406 is similar to the process described in the first embodiment. If one waveform can not be recognized in step S406, the CPU 10 repeats the process from step S402.

When one waveform can be recognized in step S406, on the other hand, the CPU 10 judges whether or not the timer counts equal or more than 10 seconds (step S408). If the counted value is less than 10 seconds, the CPU 10 again repeats the process from step S402.

If the counted timer value is judged more than 10 seconds (S408), the CPU 10 resets the timer value and restarts it (S410), and carries out a filtering process for the resistance data (S412). Specifically, through digital filtering (band-path filtering), the CPU 10 carries out waveform analysis of the resistance data using a reference conditions such as amplitude of 10Ω (Ohms) in a frequency band of 0.1 Hz through 3 Hz. The CPU 10 acquires data of both variation cycles of the resistance and amplitudes of the resistance in accordance with the process of step S412 and records them to the memory 16 (S414).

The CPU 10 carries our filtering to the R wave height of heart beats recognized at step S406 (S416). Specifically, through the filtering, for example, the CPU 10 carries out waveform analysis of the R wave height data using a reference conditions such as amplitude of more than 0.05 mV in a frequency band of 0.1 Hz through 3 Hz. The R wave height data is data showing a temporal alteration of electric potentials of the R waves (R wave height) recognized by the CPU10. In this embodiment, the temporal alteration of the R wave is dealt as waveforms, for example. The CPU 10 acquires data of both variation cycles of the R wave height and amplitudes of the R wave height in accordance with the process of step S412 and records them to the memory 16 (S418).

The variation cycles of the R wave height is calculated using the number of maximum points within a predetermined period, for example, when the temporal alteration of the R waves is represented by waveforms. Generally, it is known that R wave height may vary depending on an examinee's breathing. In this embodiment, an available factor for estimating respiration rate, variation cycle of R wave height is employed in addition to the variation cycles of the resistance of the chest respiratory information sensor 502 so on.

The CPU 10 carries out respiration rate estimating process (S500).

Figure 23:
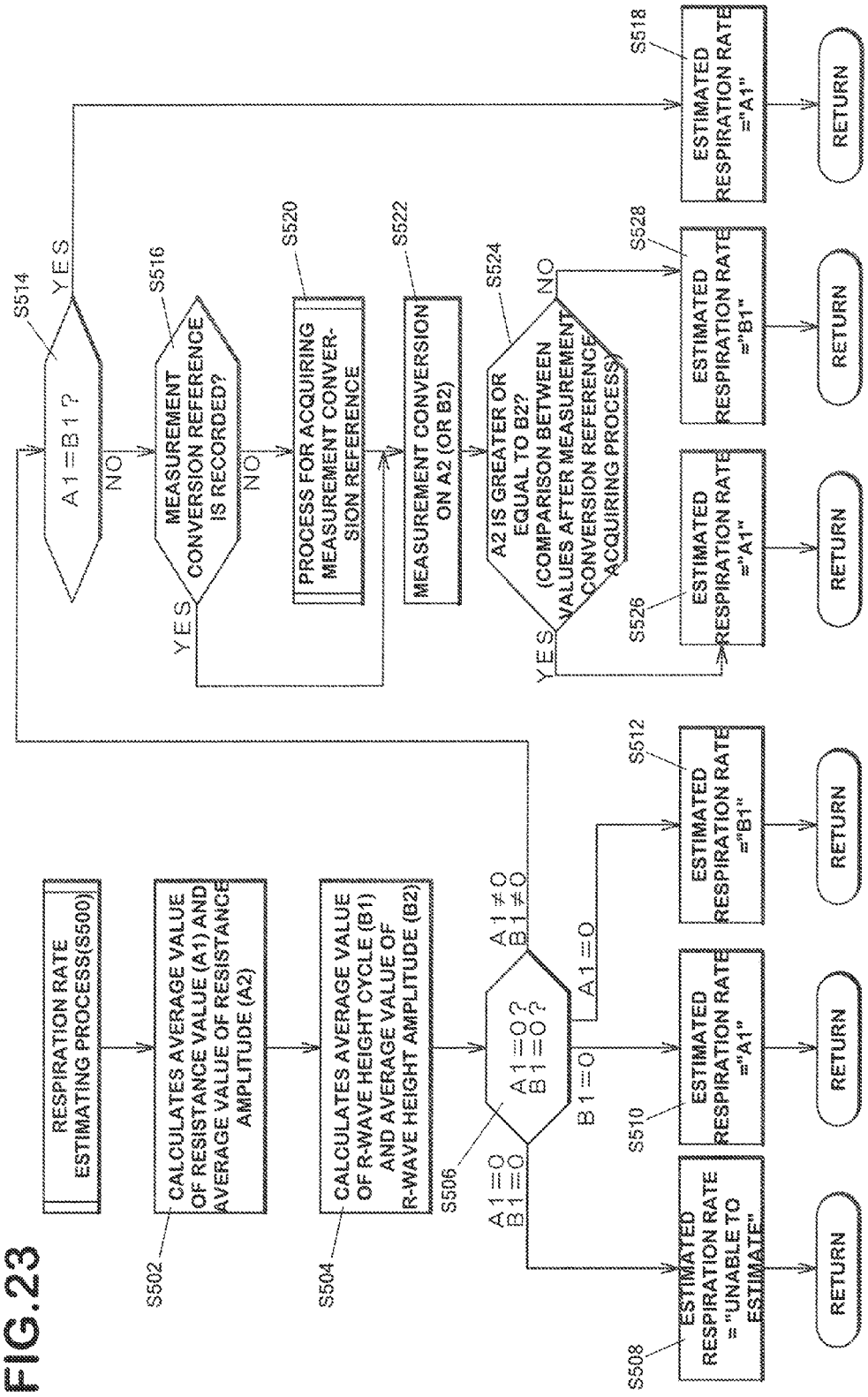
FIG. 23 is a flow chart for processing measurement of respiration rates according to the fourth embodiment.

FIG. 23 is a flowchart of a program of estimated respiration rate determination process which is indicated as a sub-routine at step S500 of FIG. 22. The CPU 10 calculates an average value of resistance value (hereinafter referred also to as "A1" for simplicity), an average value of resistance amplitude (hereinafter referred also to as "A2" for simplicity) and records to the memory 16 (S502).

Further, the CPU 10 calculates an average value of an R wave height cycle (hereinafter referred also to as "B1" for simplicity) and an average value of R wave height amplitude (hereinafter referred also to as "B2" for simplicity) and records them to the memory 16 (S504)

In the fourth embodiment, data on a plurality of R waves is obtained with a plurality of the chest lead electrodes and the four limb lead electrodes shown in FIG. 21, data about a plurality of resistance values are acquired through the chest respiratory information sensor 601 and the abdominal respiratory information sensor 602. In the following description, it is assumed that the CPU 10 selects data for one of the R waves out of the data on a plurality of the R waves and selects data for one of the resistance value out of the data on a plurality of the resistance values. For the process of selecting the data on R wave height through one lead out of a plurality of the data on R wave heights via the chest lead electrodes and the process of selecting one of the resistance data out of the resistance data of the sensors 601 and 602, a larger average value of amplitudes obtained process carried out at step S414, S418 may be used. Specifically, when a total resistance value originated from the sensor 602 is 12 and another total resistance value originated from the sensor 601 is 11.5, the CPU 10 performs the process after S500 only for the resistance value originated from the sensor 602. For the process of selecting the data on R wave height through one lead out of a plurality of the data on R wave heights via the chest lead electrodes and the four limb lead electrodes, RS amplitude values obtained at step S250 of FIG. 11 showing the cardiogram measurement processing in the second embodiment (or a total value of RS amplitude acquired at S252) may be used. Specifically, totals of the RS amplitude values within a predetermined time period for each chest lead is calculated, and selects the R wave height data originated from the largest total value chest lead and performs the process after S418.

FIG. 25A is a view showing that data record of the memory 16 in which a resistance cycle, a resistance amplitude, an R-wave height cycle, an R-wave height amplitude and the like and an average values there is shown. The term "Data No. (data number)" is the number for specifying each cycle. The CPU 10 records in the memory 16 resistance data and R-wave height data using millisecond as their measure, and records on the column of the same data number in a table shown in FIG. 25A, information (cycles, amplitudes and so on) about the data whose difference in positions of both peak values (or the bottom values) is less than a 200 mm second (see FIG. 26 for positions of the peak values and that of the bottom values so on). The resistance cycle and the R-wave height cycle are represented by amplitudes of waveform per second (measure: Hertz), for example.

The CPU 10 judges whether or not A1=0 and B1=0 is satisfied (S506). When A1=0 and B1=0 is satisfied, the CPU 10 records an estimated respiration rate as "unable to estimate" (S508) and then carries out the process from step S422 of FIG. 22. The case A1=0, B1=0 corresponds to the case in which a cycle can not be acquired as a result of a waveform analysis in the filtering of each step S412 and S416 shown in FIG. 22. Specifically, for example, in the case of electric resistance, a resistance cycle becomes 0 when a waveform including the vibration more than 10-ohms variation cannot be analyzed while the frequency band is in 0.1 through 3 Hz as a result of the signal of a frequency band 3 Hz or more being emphasized by movement of the examinee.

When B1=0 (A1 is not equal to 0) at step S506, the CPU 10 records "A1" as an estimated respiration rate (S510) and then carries out the process from step S422 of FIG. 22. When A1=0 (B1 is not equal to 0) at step S506, the CPU 10 records "B1" as an estimated respiration rate (S512) and then carries out the process from step S422 of FIG. 22. When either one of information, such as a resistance value and an R-wave height is valid, such valid information will be employed as an estimated respiration rate.

In the process of step 506, when neither of A1 and B1 equal to 0, the CPU 10 judges whether or not A1 equal to B1 (S514). When A1 equal to B1, the CPU 10 records "A1" as an estimated respiration rate (S518) and then carries out the process from step S422 of FIG. 22.

It is judged that A1 not equal to B1 at S514, the CPU 10 further judges whether or not "measurement conversion reference" described later is recorded on the memory 16 (S516). When the measurement conversion reference" is recorded on the memory 16, the CPU 10 carries out measurement conversion on A2 (or B2) (S522). Details of such conversion will be described later.

When it is judged at step S516 that the measurement conversion reference is not recorded on the memory 16, the CPU 10 carries out at step S520 the process for acquiring the measurement conversion reference.

Figure 24:
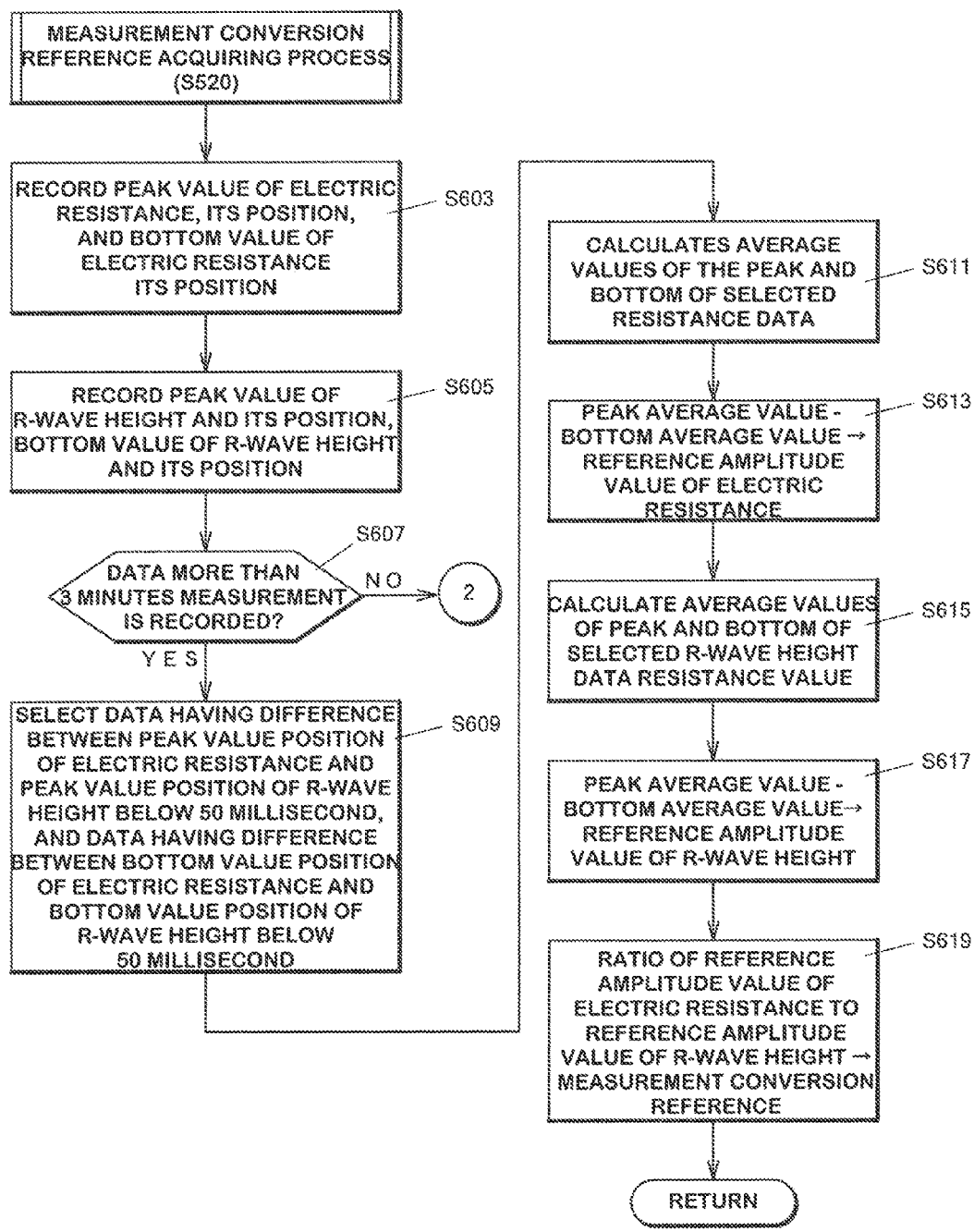
FIG. 24 is a flow chart for processing measurement of respiration rates according to the fourth embodiment.

FIG. 24 is a flowchart of a program of measurement conversion reference acquiring process which is indicated as a sub-routine at step S520 of FIG. 23. The CPU 10 calculates the peak value of electric resistance (Ω) and its position (measurement:millisecond), the bottom value of electric resistance (Ω) and its position (measurement:millisecond) in accordance with the resistance value data recorded on the memory 16 (see S402 in FIG. 22), and record them on the memory 16 (S603). Both of the peak value and the bottom value and so on correspond to the maximum value and the bottom value of each waveform cycle shown in FIG. 17.

Then the CPU 10 calculates the peak value (mV) of an R-wave height and its position (millisecond), the bottom value (mV) of an R-wave height and its position (millisecond) in accordance with the R-wave height data recorded on the memory 16 (see S404 in FIG. 22) and record on the memory 16 (S605). Waveform analysis in steps S603 and S605 utilize the filtering described in steps S412 and S414 in FIG. 22, for example. The technique for waveform analysis used in steps S412, S414 shown in FIG. 22 and steps S603, S605 of FIG. 24 is not limited to the above-described technique that is well-known to the person skilled in the art such as Wavelet, FTT (fast Fourier transformation) and the like can be used.

FIG. 26A is a view showing data record of resistance values (peak values, bottom values etc.) and the bottom values, the bottom position (information on measurement period) and R-wave height (peak value and its position, bottom value and its position) calculated by the CPU. The term "Data No." Is the number for specifying each respiration (each respiratory action).

The CPU 10 judges whether or not that data of the peak and the bottom values within a time period corresponds to more than three minutes measurement is recorded (S607). When no data for more than a three minute measurement is not recorded, the CPU 10 repeats the process from step S402 shown in FIG. 22. When data for more than a three minute measurement is not recorded, the CPU 10 selects the respiration data that has a difference between the peak value position of electric resistance and the peak value position of R wave height below 50 millisecond and that has a difference between the bottom value position of electric resistance and the bottom value position of R wave height below 50 millisecond (S609). In the case of FIG. 26A, respiration data of Data No. "1501" is an object to be selected because such data has the peak value difference of four milliseconds (=|2502 (milliseconds)−2498 (milliseconds)|) and the bottom value difference of seven milliseconds (=|4402−4395|). Similarly, respiration Data No. "1543" is also an object to be selected. In the embodiment, it is judged that data of the peak and the bottom values within a time period corresponds to more than three minutes measurement is recorded at step S607, but any other time period may also be employed. Also, the respiration data having a difference "below 50 millisecond" is selected in step S609, such difference is a reference for selecting respiration data almost corresponding to the peak (or bottom) position of electric resistance data and that of R-wave height data. Any other time period other than "below 50 millisecond" but within a range capable of selecting respiration data almost corresponding to the both may be employed.

The CPU 10 calculates an average value of the peak (peak average value) and an average value of the bottom (bottom average value) of the resistance data selected at step 609 (S611). Here, it is assumed that the respiration data contains Data No. 1501 and 1543 shown in FIG. 26A is selected. Then the CPU 10 calculates a difference between the peak average value and the bottom average value, and record the calculation result on the memory 16 as "a reference amplitude value of electric resistance" (S613).

Subsequently, the CPU calculates an average value of the peak (peak average value) and an average value of the bottom (bottom average value) of the R-wave height data resistance value selected at step S609 (S615). Then the CPU 10 calculates a difference between the peak average value and the bottom average value, and record the calculation result on the memory 16 as "a reference amplitude value of R-wave height" (S617). FIG. 26B is a view showing data record of each of the values calculated by the CPU 10 after carrying out step S617.

The CPU 10 records on the memory 16 a ratio of the reference amplitude value of electric resistance to the reference amplitude value of R-wave height as "measurement conversion reference". Here, calculation is made under an assumption that an equation measurement conversion reference=(a reference amplitude value of electric resistance)/(a reference amplitude value of R-wave height) as an example. FIG. 26C is a view showing data record of each of the values calculated by the CPU 10 after carrying out step S619. Here, it is assumed that a reference amplitude value of electric resistance=11.2 (Ω), a reference amplitude value of R-wave height (0.24 mV) and a measurement conversion reference=24 are recorded.

After performing step S619, the CPU 10 performs calculation for measurement conversion of A2 (or B2) indicated at S522 of FIG. 23. FIG. 25B is a view showing a data record of values recorded on the memory 16. Specifically, in addition to the average value of resistance amplitude (A2) calculated at step S502 of FIG. 23 and the average value of R-wave height amplitude (B2) calculated at step S504, an R-wave height amplitude after measurement conversion is recorded on the memory 16. The R-wave height amplitude after the measurement conversion is calculated by multiplying a measurement conversion reference (47, herein) (obtained through a measurement conversion process) to B2 (measurement: mV).

In the embodiment herein, the measurement conversion reference is obtained using data for more than three minutes measurement from the start, other method can also be used. For another embodiment, the measurement conversion reference may be updated continuous basis by performing a measurement conversion reference acquiring process (FIG. 24) after progress of a predetermined time period.

In the above-described embodiment, the ratio of the "reference amplitude value of electric resistance" to the "reference amplitude value of R-wave height" is employed as the measurement conversion reference, but a ratio of the "reference amplitude value of R-wave height" to the "reference amplitude value of electric resistance" may also be employed. Alternatively, the measurement conversion reference acquiring process (FIG. 24) may be omitted by setting a fixed factor as a measurement conversion reference.

The CPU 10 judges whether or not A2 is greater or equal to the B2 after conversion (S524). When it is judged that A2 is greater than B2, the CPU 10 records "A1" as an estimated respiration rate (S526), and then carries out the process from step S422 of FIG. 22. When it is judged that A2 is less than B2, the CPU 10 records "B1" as an estimated respiration rate (S528), and then carries out the process from step S422 of FIG. 22. By performing a process for obtaining a measurement conversion reference (step S520 of FIG. 23) and processes S522, S524, S526 and S528 described in the above, when the average value of the electric resistance cycle (A2) and that of R-wave height amplitude cycle (B2) are different from each other, the one corresponding to having a large amplitude (average amplitude value in the predetermined time period) is selected from the both average values. After selecting the one corresponding to having a larger amplitude out of the resistance amplitude and the R-wave height amplitude, generally respiratory operation to the examinee is acquirable with sufficient sensitivity by adopting the cycle as an estimated respiratory rate.

After carrying out process of determining the estimated respiration rate shown in S500, the CPU 10 outputs to the display 14 the respiration values according to the estimated value recorded on the memory 16 (S422). Here, since the estimated number is a cycle (measurement: Hertz), the CPU 10 performs a calculation that an estimated respiration ×60 when a respiration rate (for 1 minute) is output. For example, in the case of data shown in FIG. 25B, it is judged that A2 is less than B2 at the step S524 of FIG. 23, so "0.25 (an average value of the R-wave height cycle shown in FIG. 25A)" is recorded as an estimated respiration value. In this case, the CPU 10 displays 15 (=0.25×60) as a respiration value on the display 14.

Figure 27:
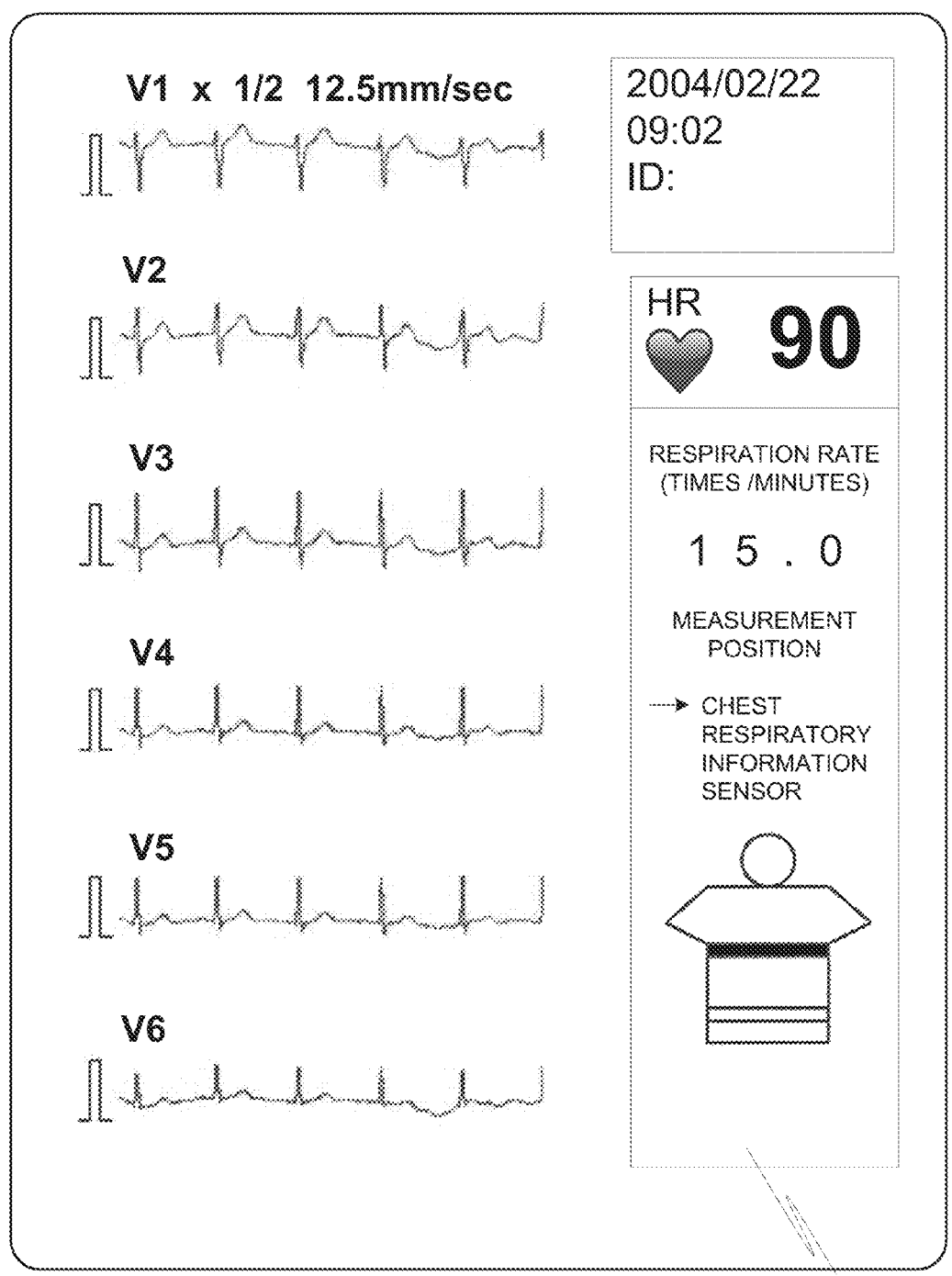
FIG. 27 is display examples of data under processing of respiration rate measurement according to the fourth embodiment.

FIG. 27 shows display examples on the display 14 which are under processing of respiration rate measurement according to the fourth embodiment. On a respiratory information display area 650, a respiration rate, a position (measurement position) based on measurement of the respiration rate are displayed. The displayed measurement position is the one used for measuring the respiration rate which is selected from the selections such as the chest lead set 603, the four limb lead set 604, the chest respiratory information sensor 601 and the abdominal respiratory information sensor 602 shown in FIG. 21. When the R-wave amplitude shown in FIG. 25B is originated by the abdominal respiratory information sensor 602, "measurement position: abdominal respiratory information sensor" is displayed on the respiratory information display area 650. Other display method may also be employed, for example, a display method similar to the measurement position guide 480 shown in FIG. 13A (a method in which the measurement position is displayed on a diagram of the examinee's body so as to physically corresponding to the position to the body) can be employed.

6-3. Advantage of the Embodiment

In the above-described embodiment, respiration values are measured using information on variation of R-wave height acquired from the chest electrodes and the four limb lead electrodes in addition to information on variation of the electric resistance of the chest respiratory information sensor 601 (or the abdominal respiratory information sensor 602). Consequently, respiration value can be measured by selectively using the information on the R-wave height variation even when the information on variation of the resistance is not reflecting respiratory operation correctly by considering the examinee's movement as a cause.

6-4. Variation of the Fourth Embodiment

In the fourth embodiment, while "respiration value" is illustrated as an example of the output of the respiration rate measurement processing, other outputs can be used. In another output, "depth of respiration" may also be output. For example, generally, each of the resistance value obtained at step S414 of FIG. 22 or the R-wave amplitude is in proportion to depth of respiration of the examinee. Specifically, the deeper the depth of respiration, the larger the variation of the girth-of-the-chest length (a length of the chest respiratory information sensor 601), so that the resistance value is increased. Consequently, depth of respiration can be calculated according to a ratio of a resistance amplitude value (or an R-wave height amplitude) under measurement to a ratio of a resistance amplitude value (an R-wave height amplitude) at a normal state of the examinee. In this way, it is possible to acquire information on depth of respiration during the circumstances such as in motion, after motion, or in asthma, or under sleep so on.

7. Other Embodiments

In the above-description, the first through the fourth embodiments are described as independent embodiments, but this is not only the way, the present invention may also be embodied by combining technical components included in each of the embodiments. For example, in an embodiment combining the first (or the second) embodiment and the third (or the fourth) embodiment with the first (or the second) embodiment with the third (or the fourth) embodiment, measurement of a cardiogram and that of respiration value can be performed at the same time.

In the above-described embodiments, the program for operation of the CPU 10 is stored in the F-ROM 17. Storage of the program is not limited to that place, other data storage means including hard-disks and the like may also be used. The program for operation of the CPU 10 may be installed in hard-disks and the like upon reading out from a CD-ROM in which the program being recorded therein. The program can be installed from a computer readable data storage medium such as a DVD-ROM, or a flexible disc (FD), or an IC card beside the CD-ROM. In addition, such program can be downloaded via a communication line. By installing the program from a CD-ROM, direct execution of the program stored in the CD-ROM may be done instead of performing indirect execution of the program by executing the program with a computer.

The program executable with the computer is not only a program executed by the CPU, other programs such as a source format program, a program once converted in other format (for example, a data compressed program, decoded program), further including a program executable in combination of other module(s).

In the above-described embodiments, each of the functions shown in FIG. 2 are realized with the CPU and the program, the entire or a part of the functions may be realized by hardware logic (logic circuitry).

What is claimed is:

1. A respiratory information analysis device comprising:
a memory; and
a CPU, the CPU adapted to:
acquire electrical information delivered from a plurality of respiratory information measuring sensors arranged on a garment adapted to measure biological information;
compare a plurality of amplitudes of the acquired electric information;
select respiratory information measuring sensors that are detecting a larger amplitude as electric information for an output of respiratory information in accordance with the comparison;
judge a variation cycle of the electric information detected with the selected respiratory information measuring sensors and analyze respiratory information in accordance with the variation cycle; and
output respiratory information data in accordance with the analyzed respiratory information.

2. The respiratory information analysis system of claim 1, further comprising acquiring information on a variation cycle of the electric information and information on an R-wave height cycle related to a variation cycle of R-wave height information of a cardiogram based on electric potentials delivered from chest lead electrodes; and selecting cycle information of either one based on an amplitude and analyzing respiratory information in accordance with the selected cycle information.

3. The respiratory information analysis system of claim 2, further comprising acquiring information on amplitude of the electric information and information on R-wave height amplitude related to amplitude of the R-wave height information and selecting one of the electric information and the R-wave height information in accordance with a comparison of the amplitudes of the electric information and the R-wave height information and analyzing respiratory information in accordance with the selected cycle information.

4. The respiratory information analysis system of claim 2, further comprising displaying one of a position of the chest lead electrodes and a position of the respiratory information measuring sensor detecting the selected information correspondingly with one of a diagram of the biological information measuring garment and a diagram of the examinee's body.

5. A method of controlling a respiratory information analysis device comprising:
acquiring electric information delivered from a plurality of respiratory information measuring sensors capable of acquiring electric information based on a variation of electric potential, the sensors including a conductive material adapted to vary its electrical resistance according to a variation of a constitution of an examinee through breathing thereof under a turning-on-electricity state;
comparing a plurality of amplitudes of the acquired electric potential information;
selecting respiratory information measuring sensors that are detecting a larger amplitude as electric information for an output of respiratory information in accordance with the comparison; and
outputting respiratory information data in accordance with the analyzed respiratory information.

6. A non-transitory computer-readable information storage media having stored thereon instructions, that when executed, perform a method for controlling a respiratory information analysis device comprising:
acquiring electric information delivered from a plurality of respiratory information measuring sensors capable of acquiring electric information based on a variation of electric potential, the sensors including a conductive material adapted to vary its electrical resistance according to a variation of a constitution of an examinee through breathing thereof under a turning-on-electricity state;
comparing a plurality of amplitudes of the acquired electric potential information;
selecting respiratory information measuring sensors that are detecting a larger amplitude as electric information for an output of respiratory information in accordance with the comparison; and
outputting respiratory information data in accordance with the analyzed respiratory information.

* * * * *